US008163748B2

(12) United States Patent
Kallenbach et al.

(10) Patent No.: US 8,163,748 B2
(45) Date of Patent: Apr. 24, 2012

(54) S-TRIAZINE COMPOUNDS, PHARMACEUTICAL COMPOSITIONS AND METHOD OF USING THE SAME

(75) Inventors: Neville Robert Kallenbach, Philadelphia, PA (US); Young-Tae Chang, Singapore (SG); Zhigang Liu, New York, NY (US); Chunhui Zhou, Woodhaven, NY (US); Jaeki Min, Marietta, GA (US)

(73) Assignee: New York University, New York, NY (US)

( * ) Notice: Subject to any disclaimer, the term of this patent is extended or adjusted under 35 U.S.C. 154(b) by 485 days.

(21) Appl. No.: 12/154,696

(22) Filed: May 23, 2008

(65) Prior Publication Data

US 2009/0325966 A1 Dec. 31, 2009

Related U.S. Application Data

(60) Provisional application No. 60/931,514, filed on May 23, 2007.

(51) Int. Cl.
*A61K 31/53* (2006.01)
*C07D 251/54* (2006.01)
*C07D 403/00* (2006.01)
(52) U.S. Cl. ......... 514/245; 544/196; 544/197; 544/198
(58) Field of Classification Search .................. 514/245; 544/196–198
See application file for complete search history.

(56) References Cited

U.S. PATENT DOCUMENTS

2004/0122009 A1 6/2004 Chang et al.

FOREIGN PATENT DOCUMENTS

WO 9936410 7/1999

OTHER PUBLICATIONS

Silen et al. "Screening for novel antimicrobials from encoded combinatorial libraries by using a two-dimentional agar fromat," Antimicrobial Agents and Chemotherapy, 1998, vol. 42, No. 6, pp. 1447-1453.*
Zasloff, M., "Antimicrobial peptides of multicellular organisms," Nature, Jan. 24, 2002; 415(6870):389-05.
Boman, H.G., "Antibacterial peptides: basic facts and emerging concepts," Journal of Internal Medicine, 2003, 254 (3):197-2115.

(Continued)

*Primary Examiner* — Shengjun Wang
(74) *Attorney, Agent, or Firm* — Klauber & Jackson LLC

(57) ABSTRACT

Novel s-triazine compounds are disclosed that have a formula represented by the following:

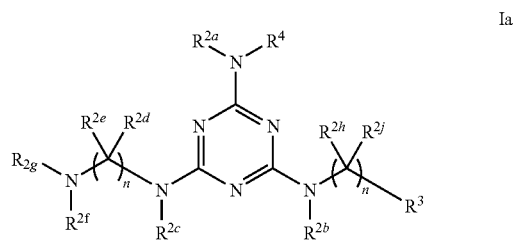

The compounds may be prepared as pharmaceutical compositions, and may be used for the prevention and treatment of a variety of conditions in mammals including humans, where microbial infection is either a direct cause or a related condition.

17 Claims, 1 Drawing Sheet

OTHER PUBLICATIONS

Medzhitov, R. and C. Janeway, Jr. 2000. Innate immune recognition: mechanisms and pathways, Immunol. Rev. 173:89-97.
Brogden, K. A., Ackermann, M., McCray, P. B., and Tack, B. F. 2003, "Antimicrobial peptides in animals and their role in host defences," Int J Antimicrob Agents 22(5):465-78.
Hancock, R.E., 1999, "Host defence (cationic) peptides: what is their future clinical potential?" Drugs 57(4):469-73.
Fischetti, V.A., 2003, "Novel method to control pathogenic bacteria on human mucous membranes," Ann. N. Y. Acad. Sci. 987:207-14.
Yeaman, M. R. and Yount, N.Y., 2003, "Mechanisms of antimicrobial peptide action and resistance," Pharmacol Rev. 55:27-55.
Strøm, M. B., Haug, B. E., Skar, M. L., Stensen, W., Stiberg, T. and Svendsen, J.S., 2003, "The pharmocophore of short cationic antibacterial peptides," J. Med. Chem. 46(9):1567-1570.
Liu, Z., Brady, A., Young, A., Rasimick, B., Chen, K., Zhou, C. and Kallenbach, N. R. 2007, "Length effects in antimicrobial peptides of the (RW)n Series," Antimicrobial Agents and Chemotherapy 51(2):597-603.
Arvidsson, P. I., Frackenpohl, J., Ryder, N. S., Leichty, B., Petersen, F., Zimmermann, H., Camenisch, G. P., Woessner, R. and Seebach, D., 2001, "On the antimicrobial and hemolytic activities of amphiphilic β-peptides," ChemBioChem 2(10):771-773.
Goodson, B., Ehrhardt, A., Ng, S., Nuss, J., Johnson, K., Giedlin, M., Yamamoto, R., Moos, W. H., Krebber, A., Ladner, M., Giacona, M. B., Vitt, C. and Winter, J.,1999, "Characterization of novel antimicrobial peptoids," Antimicrobial Agents and Chemotherapy 43(6):1429-1434.
Rennie, J., Arnt, L., Tang, H., Nuesslein, K. and Tew, G. N., 2005, "Simple oligomers as antimicrobial peptide mimics," J. Industrial Microbiology & Biotech. 32(7):296-300.
Giacometti, A., Cirioni, O., Greganti, G., Quarta, M. and Scalise, G., 1998, "In vitro activities of membrane-active peptides against gram-positive and gram-negative aerobic bacteria," Antimicrobial Agents and Chemotherapy 42 (12):3320- 3324.
Giacometti, A., Cirioni, O., Barchiesi, F., Del Prete, M. S. and Scalise, G. 1999, "Antimicrobial activity of polycationic peptides,"Peptides 20(11):1265-1273.
Huang, H.W., 2000, ".Action of antimicrobial peptides: two-state model," Biochemistry 39(29):8347-8352.

* cited by examiner

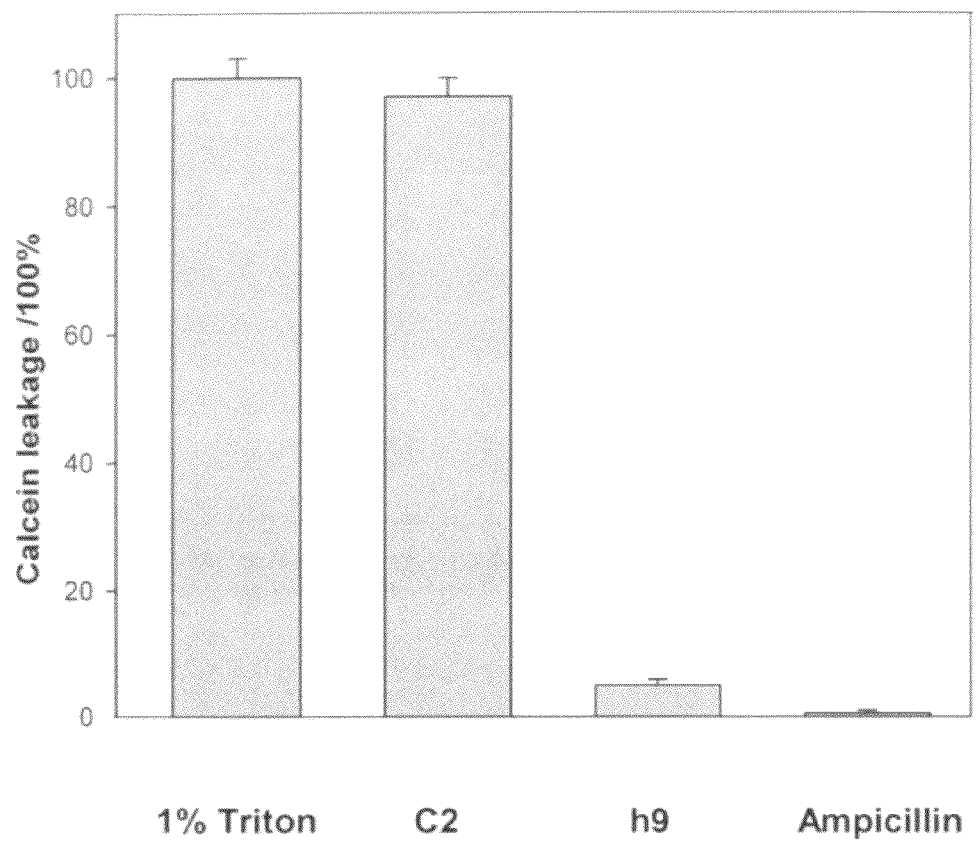

S-TRIAZINE COMPOUNDS, PHARMACEUTICAL COMPOSITIONS AND METHOD OF USING THE SAME

RELATED APPLICATION

The present application claims the benefit under 35 U.S.C. §119 of U.S. Provisional Application Ser. No. 60/931,514 filed May 23, 2007, the contents of which application is hereby incorporated by reference in its entirety.

GOVERNMENT SUPPORT

This invention was made at least in part, with government support under Grant No. N00014-03-1-0129 awarded by the Office of Naval Research. Accordingly, the United States Government has certain rights in the invention.

FIELD OF THE INVENTION

This invention relates to novel compositions containing active s-triazine compounds, and particularly, such s-triazine compounds as demonstrate antimicrobial, antifungal or antiviral activity. The invention also relates to methods for the preparation of the peptide compositions, and their use in preventing and/or treating conditions resulting from the unwanted presence of microbial, fungal or viral activity.

BACKGROUND OF THE INVENTION

As multidrug-resistant bacterial strains emerge in increasing numbers, the need for new kinds of antibiotics is growing. For the last few decades it has been found that a wide range of antimicrobial peptides are secreted by multicellular organisms in response to infection by foreign bacteria, viruses, or fungi (1-4). These form part of the innate immune response to infection, which is short term and fast acting relative to humoral immunity (3). These peptides have been considered as prospective antibiotic agents because their effect is rapid, broad spectrum and indifferent to resistance to standard antibiotics such as penicillin (5-6). Antimicrobial peptides differ dramatically in size, sequence and structure, apparently sharing only amphipathic character and positive charge (1, 5). The proposed mechanisms of action of antimicrobial peptides commonly focus on the interaction between these peptides and the plasma membrane of bacterial cells, even though many antimicrobial peptides also employ more sophisticated mechanisms (7). Recently, the pharmocophore of short cationic antimicrobial peptides has been extensively studied and the results showed that short cationic peptides consisting of only Arginine (R) and Tryptophan (W) could serve as moderately effective antimicrobial agents (8-9).

Besides various advantages over conventional antibiotics, the practical use of antimicrobial peptides, however, are limited by many factors. These peptides are usually more expensive to make, vulnerable to protease degradation, and have relatively high toxicity. A number of nonnatural peptides built from beta-amino acids or peptoids, as well as other peptide mimics have been studied in order to overcome these problems (10-12). In this study, we designed and screened inexpensive small compounds to mimic the hydrophobic-cationic pattern observed in the pharmocophore of small cationic antimicrobial peptides using 1,3,5-triazine as a template. Previous studies showed that possible antimicrobials could be identified through combinatorial libraries constructed to have varieties of tri-substituted 1,3,5-triazines (13).

From the above, it remains that a continuing need exists for the stepwise design and optimization of different functional groups (mainly hydrophobic, bulky or charged groups) on the triazine scaffold in search of potential new antimicrobials, as well as to gain insight as to the structure-function relationship of these agents.

Furthermore, it remains that a continuing need exists for the development of modalities that can deliver effective antibiotic s-triazine compounds in a manner that confers both improved stability and economy of the therapeutic, but importantly, significantly improves the therapeutic efficacy and strength of the resultant molecule. It is toward the fulfillment of these and other related objectives that the present invention is directed.

SUMMARY OF THE INVENTION

As set forth earlier herein, the present invention relates to s-triazine compounds, pharmaceutical compositions thereof and their use as antimicrobial/antiviral/antifungal compounds.

The present invention relates to s-triazine compounds having antimicrobial properties, according to formula I:

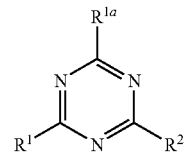

wherein
each $R^1$, $R^{1a}$ and $R^2$ is independently substituted amino; or a pharmaceutically acceptable salt, solvate or prodrug thereof; and stereoisomers, isotopic variants and tautomers thereof.

More particularly, the present invention relates to s-triazine compounds having antimicrobial properties, according to formula Ia:

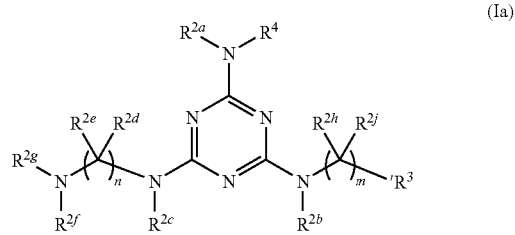

wherein
each of $R^{2a}$, $R^{2b}$, $R^{2c}$, $R^{2d}$, $R^{2e}$, $R^{2f}$, $R^{2g}$, $R^{2h}$ and $R^{2j}$ is independently selected from hydrogen, and substituted or unsubstituted $C$—$C_6$ alkyl; or any two of $R^{2c}$, $R^{2d}$, $R^{2e}$, $R^{2f}$ and $R^{2g}$ may join together to form a cycloalkyl or cycloheteroalkyl ring or 3-7 atoms;

$R^3$ is $R^4$ or substituted or unsubstituted $C_1$-$C_6$ alkyl; or is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;

$R^4$ is

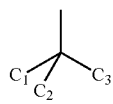

wherein $C^1$, $C^2$ and $C^3$ taken together with the C atom to which they are attached to form a bi- or tri-cyloalkyl or cycloheteroalkyl ring system of 7-13 atoms; and wherein the ring system is substituted or unsubstituted;
m is 0, 1, 2 or 3; and n is 2, 3 or 4;
or a pharmaceutically acceptable salt, solvate or prodrug thereof;
and stereoisomers, isotopic variants and tautomers thereof.

In one embodiment, with respect to compounds of formula Ia, $R^4$ is substituted or unsubstituted

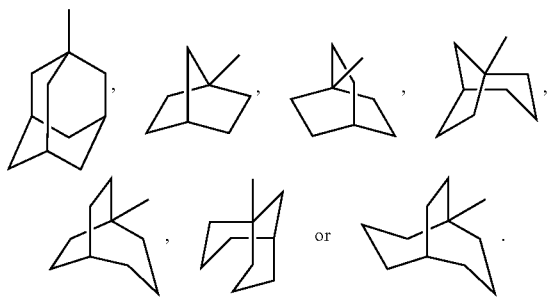

In a preferred embodiment, with respect to compounds of formula Ia, $R^4$ is adamantane.

In a preferred embodiment, with respect to s-triazine compounds of formula Ia, each $R^{2b}$, $R^{2d}$, $R^{2e}$, $R^{2h}$ and $R^{2j}$ is hydrogen.

In one embodiment, with respect to s-triazine compounds of formula Ia, each $R^{2f}$ and $R^{2g}$ is Me, Et or n-Bu. In a preferred embodiment, each $R^{2f}$ and $R^{2g}$ is n-Bu.

In one embodiment, with respect to s-triazine compounds of formula Ia, n is 2 or 3. In a preferred embodiment, n is 3.

In one embodiment, with respect to s-triazine compounds of formula Ia, m is 0, 1 or 2.

In one embodiment, with respect to s-triazine compounds of formula Ia, $R^4$ is cycloheptyl, cyclohexyl or phenyl.

In a further aspect, the present invention provides the method for the preparation of the s-triazine compounds of the invention.

In a further aspect, the s-triazine compounds of the invention may be used to treat microbial or fungal conditions affecting lower animals, and possibly, plants. The s-triazine compounds could be designed and assembled to include the s-triazine compounds pertinent for the treatment of a particular microbe or fungus of interest, and then formulated into appropriate compositions and dosage forms for administration or application to an affected host.

In a further aspect, the present invention provides pharmaceutical compositions comprising a peptide of the invention, and a pharmaceutical carrier, excipient or diluent. In this aspect of the invention, the pharmaceutical composition can comprise one or more variant s-triazine compounds of the invention, prepared, for example, with a differing array of peptide linkers, to afford a more comprehensive treatment in the instance where a multiplicity of microbial/viral/fungal antigens are known to be present.

In a further aspect of the invention, a method is disclosed for treating mammals, including humans, as well as lower mammalian species, susceptible to or afflicted with a condition attributable to or resulting from amicrobial, viral or fungal infection, which method comprises administering an effective amount of a pharmaceutical composition containing or comprising the s-triazine compounds just described.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description, which proceeds with reference to the following illustrative drawings.

BRIEF DESCRIPTION OF THE DRAWINGS

FIG. 1 graphically depicts the results of the measurement of the ability of a triazine compound of the invention to induce leakage of calcein, entrapped within the interior of large unilamellar vesicles of model membrane POPG. The extent of leakage of encapsulated calcein was detected by its fluorescence at 515 nm, with 100% leakage calibrated by addition of 0.2% Triton X-100.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR$^{21}$C(O)$R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)$R^{23}$ where $R^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-$NR^{28}R^{29}$, wherein each of $R^{28}$ and $R^{29}$ are independently selected from hydrogen and alkyl.

"Arylamino" refers to the group aryl-$NR^{30}R^{31}$, wherein each of $R^{30}$ and $R^{31}$ are independently selected from hydrogen, aryl and heteroaryl.

"Alkoxyamino" refers to a radical —N(H)O$R^{32}$ where $R^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —$NR^{33}R^{34}$ where $R^{33}$ represents an alkyl or cycloalkyl group and $R^{34}$ is an aryl as defined herein.

"Alkylsulfonyl" refers to a radical —S(O)$_2R^{35}$ where $R^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)$R^{35}$ where $R^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —S$R^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —$NH_2$.

"Substituted amino" includes those groups recited in the definition of "substituted" herein, and particularly refers to the group —N($R^{36}$)$_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N($R^{36}$)$_2$ is an amino group.

"Aminocarbonyl" refers to the group —C(O)$NR^{37}R^{37}$ where each $R^{37}$ is independently hydrogen, alkyl, aryl and cycloalkyl, or where the $R^{37}$ groups are joined to form an alkylene group.

"Aminocarbonylamino" refers to the group —$NR^{38}$C(O)$NR^{38}R^{38}$ where each $R^{38}$ is independently hydrogen, alkyl, aryl or cycloalkyl, or where two R groups are joined to form an alkylene group.

"Aminocarbonyloxy" refers to the group —OC(O)$NR^{39}R^{39}$ where each $R^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NH$R^{40}$ where $R^{40}$ represents an aryl group as defined herein.

"Aryloxycarbonyl" refers to a radical —C(O)—O-aryl where aryl is as defined herein.

"Arylsulfonyl" refers to a radical —S(O)$_2R^{41}$ where $R^{41}$ is an aryl or heteroaryl group as defined herein.

"Azido" refers to the radical —$N_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N($R^{42}$)$_2$ where each $R^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —O$R^{43}$ where $R^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O—, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{43}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$ where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following:

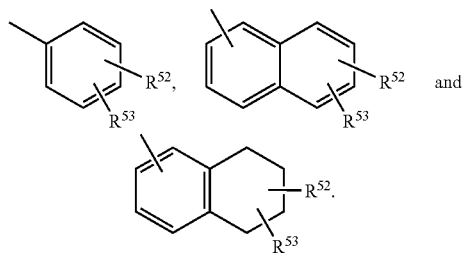

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, het-eroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

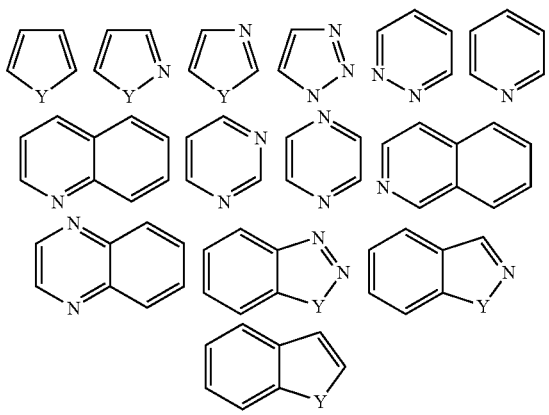

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

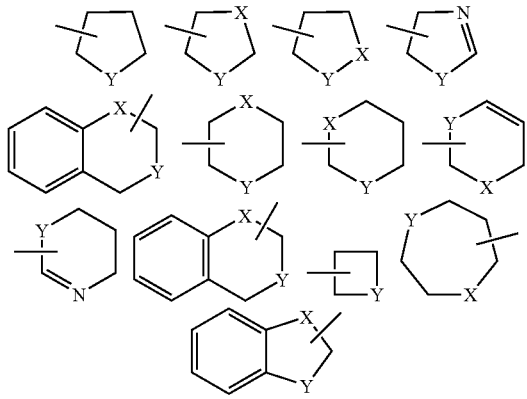

wherein each X is selected from $CR^{58}$, $CR^{58}{}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

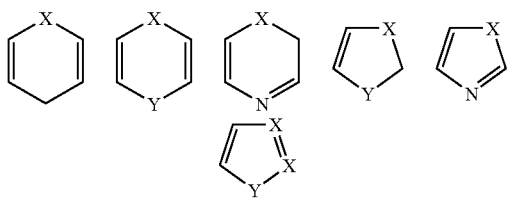

wherein each X is selected from $CR^{58}$, $CR^{58}{}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

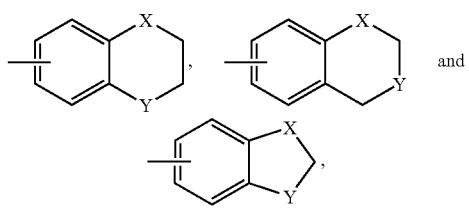

wherein each X is selected from C—$R^{58}{}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R group present as substituents directly on the ring atoms of the compounds provided herein or may be present as a substituent in the "substituted" aryl and aliphatic groups present in the compounds.

Examples of hetero substituents include:
-halo,
—$NO_2$, —$NH_2$, —$NHR^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{19}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Hydrogen bond donor" group refers to a group containg O—H, or N—H functionality. Examples of "hydrogen bond donor" groups include —OH, —$NH_2$, and —NH—$R^{59a}$ and wherein $R^{59a}$ is alkyl, acyl, cycloalkyl, aryl, or heteroaryl.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —$SR^{60}$ where $R^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as $R^{61}$—(O$_2$)S— wherein $R^{61}$ is any substituent described herein. "Aminosulfonyl" or "Sulfonamide" refers to the radical H$_2$N(O$_2$)S—, and "substituted aminosulfonyl" or "substituted sulfonamide" refers to a radical such as $R^{62}{}_2$N(O$_2$)S— wherein each $R^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound provided herein that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound provided herein is administered.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2H$ or D), carbon-13 ($^{13}C$), nitrogen-15 ($^{15}N$), or the like. It will be understood that, in a compound comprising an unnatural proportion of an isotope, any example of an atom where present, may vary in isotope composition. For example, any hydrogen may be $^2H/D$, or any carbon may be $^{13}C$, or any nitrogen may be $^{15}N$, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds provided herein may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The S-Triazine Compounds

As set forth earlier herein, the s-triazine compounds comprise antimicrobial/antiviral/antifungal s-triazine compounds. The s-triazine compounds may have a lethal effect on bacteria, viruses or fungi in its monomeric form. More particularly, the s-triazine compounds may be any antimicrobial s-triazine compounds, including natural products found in organisms, fragments of natural s-triazine compounds, and any synthetic analogs or de novo designs. These s-triazine compounds can accordingly include normatural amino acids: beta-amino acids, d-amino acids and/or non-indigenous amino acids.

The present invention relates to s-triazine compounds having antimicrobial properties, according to formula I:

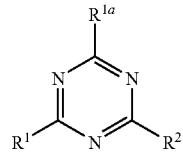

wherein
each $R^1$, $R^{1a}$ and $R^2$ is independently substituted amino; or a pharmaceutically acceptable salt, solvate or prodrug thereof; and stereoisomers, isotopic variants and tautomers thereof.

More particularly, the present invention relates to s-triazine compounds having antimicrobial properties, according to formula Ia:

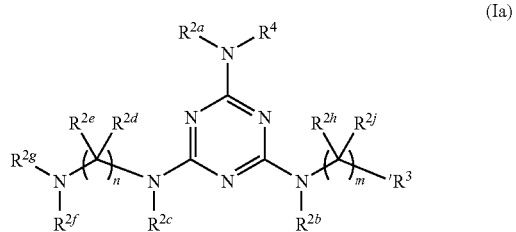

wherein
each of $R^{2a}$, $R^{2b}$, $R^{2c}$, $R^{2d}$, $R^{2e}$, $R^{2f}$, $R^{2g}$, $R^{2h}$ and $R^{2j}$ is independently selected from hydrogen, and substituted or unsubstituted $C_1$-$C_6$ alkyl; or any two of $R^{2c}$, $R^{2d}$, $R^{2e}$, $R^{2f}$ and $R^{2g}$ may join together to form a cycloalkyl or cycloheteroalkyl ring or 3-7 atoms;
$R^3$ is $R^4$ or substituted or unsubstituted $C_1$-$C_6$ alkyl; or is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;
$R^4$ is

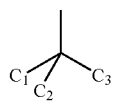

wherein $C^1$, $C^2$ and $C^3$ taken together with the C atom to which they are attached to form a bi- or tri-cyloalkyl or cycloheteroalkyl ring system of 7-13 atoms; and wherein the ring system is substituted or unsubstituted; m is 0, 1, 2 or 3; and n is 2, 3 or 4;
or a pharmaceutically acceptable salt, solvate or prodrug thereof;
and stereoisomers, isotopic variants and tautomers thereof.

In one embodiment, with respect to compounds of formula Ia, $R^4$ is substituted or unsubstituted

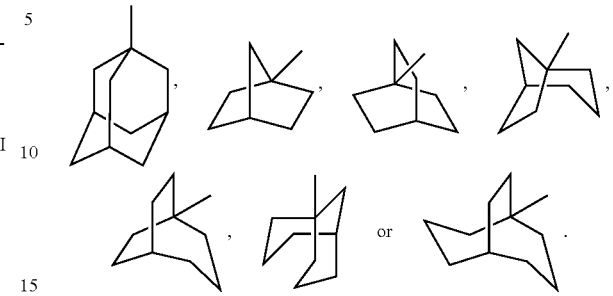

In one embodiment, with respect to compounds of formula I, $R^4$ is

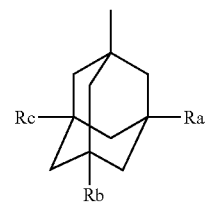

and wherein $R^a$, $R^b$ and $R^c$ are independently selected from H, halo, hydroxyl, alkyl, amino, and aryl.

In one embodiment, with respect to compounds of formula Ia, $R^4$ is as described above and each $R^a$, $R^b$ and $R^c$ is independently selected from H, Br, Cl, OH, Me, NHAc, Ph and F. In a preferred embodiment, each $R^a$, $R^b$ and $R^c$ is H.

In one embodiment, with respect to compounds of formula Ia, each $R^{2a}$, $R^{2b}$, $R^{2c}$, $R^{2d}$, $R^{2e}$, $R^{2f}$, $R^{2g}$, $R^{2h}$ and $R^{2j}$ is independently hydrogen.

In one embodiment, with respect to compounds of formula Ia, one of $R^{2a}$, $R^{2b}$, $R^{2c}$, $R^{2d}$, $R^{2e}$, $R^{2f}$, $R^{2g}$, $R^{2h}$ and $R^{2j}$ is substituted or unsubstituted $C_1$-$C_6$ alkyl and the rest are hydrogen.

In one embodiment, with respect to compounds of formula Ia, one of $R^{2a}$, $R^{2b}$, $R^{2c}$, $R^{2d}$, $R^{2e}$, $R^{2f}$, $R^{2g}$, $R^{2h}$ and $R^{2j}$ is methyl and the rest are hydrogen.

In one embodiment, with respect to compounds of formula Ia, each of $R^{2c}$, $R^{2d}$, and $R^{2f}$ is hydrogen and $R^{2e}$, and $R^{2g}$ are joined together to form a 4-7 membered heterocycloalkyl ring.

In one embodiment, with respect to compounds of formula Ia, $R^{2b}$ is substituted or unsubstituted $C_1$-$C_6$ alkyl.

In one embodiment, with respect to compounds of formula Ia, $R^{2b}$ is methyl, ethyl, or propyl.

Another aspect of invention provides a s-triazine compound having a formula:

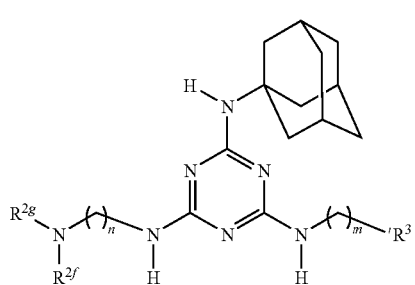

wherein
each of $R^{2f}$, and $R^{2g}$ is independently selected from hydrogen, and substituted or unsubstituted $C_1$-$C_6$ alkyl;
$R^3$ is $R^4$ or substituted or unsubstituted $C_1$-$C_6$ alkyl; or is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;
m is 0, 1, 2 or 3; and n is 2, 3 or 4;
or a pharmaceutically acceptable salt, solvate or prodrug thereof;
and stereoisomers, isotopic variants and tautomers thereof.

In one embodiment, with respect to compounds of formula II, n is 2, 3 or 4.

In one embodiment, with respect to compounds of formula II, n is 2 or 3.

In one embodiment, with respect to compounds of formula II, n is 3.

In one embodiment, with respect to compounds of formula II, each of $R^{2f}$ and $R^{2g}$ is independently selected from hydrogen, and substituted or unsubstituted $C_1$-$C_6$ alkyl.

In one embodiment, with respect to compounds of formula II, each of $R^{2f}$ and $R^{2g}$ is hydrogen.

In one embodiment, with respect to compounds of formula II, one of $R^{2f}$ and $R^{2g}$ is hydrogen, and the other is substituted or unsubstituted $C_1$-$C_6$ alkyl.

In one embodiment, with respect to compounds of formula II, one of $R^{2f}$ and $R^{2g}$ is hydrogen, and the other is methyl, ethyl, n-propyl or n-butyl.

In one embodiment, with respect to compounds of formula II, each of $R^{2f}$ and $R^{2g}$ is independently substituted or unsubstituted $C_1$-$C_6$ alkyl.

In one embodiment, with respect to compounds of formula II, each of $R^{2f}$, and $R^{2g}$ is independently methyl, ethyl, n-propyl or n-butyl.

In one embodiment, with respect to compounds of formula II, each of $R^{2f}$ and $R^{2g}$ is methyl, ethyl, n-propyl or n-butyl.

In one embodiment, with respect to compounds of formula II, each of $R^{2f}$ and $R^{2g}$ is n-butyl.

In one embodiment, with respect to compounds of formula II, wherein m is 0.

In one embodiment, with respect to compounds of formula II, wherein m is 1.

In one embodiment, with respect to compounds of formula II, wherein m is 2.

In one embodiment, with respect to compounds of formula II, wherein m is 3.

In one embodiment, with respect to compounds of formula II, wherein $R^3$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamide.

In one embodiment, with respect to compounds of formula II, $R^3$ is selected from 3-13 membered cycloalkyl ring.

In one embodiment, with respect to compounds of formula II, $R^3$ is cyclopropyl or cyclobutyl.

In one embodiment, with respect to compounds of formula II, $R^3$ is cyclopentyl or cyclohexyl.

In one embodiment, with respect to compounds of formula II, $R^3$ is cycloheptyl.

In one embodiment, with respect to compounds of formula II, $R^3$ is $R^4$ and $R^4$ is as described for formula Ia.

In one embodiment, with respect to compounds of formula II, $R^3$ is $R^4$ and $R^4$ is selected from substituted or unsubstituted

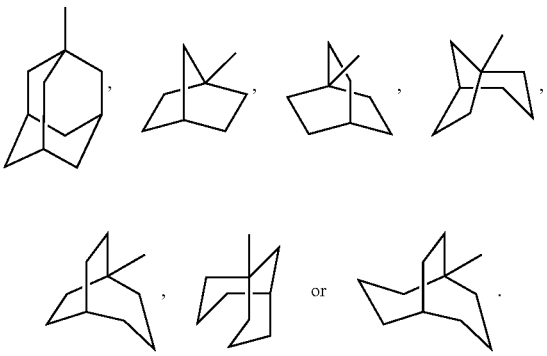

In one embodiment, with respect to compounds of formula II, $R^3$ is adamantane ring.

In one embodiment, with respect to compounds of formula II, $R^3$ is norbornane ring.

In one embodiment, with respect to compounds of formula II, $R^3$ is substituted or unsubstituted $C_1$-$C_6$ alkyl.

In one embodiment, with respect to compounds of formula II, $R^3$ is methyl, ethyl, n-propyl or n-butyl.

In one embodiment, with respect to compounds of formula II, $R^3$ is selected from a 6-13 membered aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamide.

In one embodiment, with respect to compounds of formula II, $R^3$ is phenyl, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamide.

In one embodiment, with respect to compounds of formula II, $R^3$ is unsubstituted phenyl.

In one embodiment, with respect to compounds of formula II, the compound is a quaternary salt.

In one embodiment, with respect to compounds of formula II, the compound is selected from:

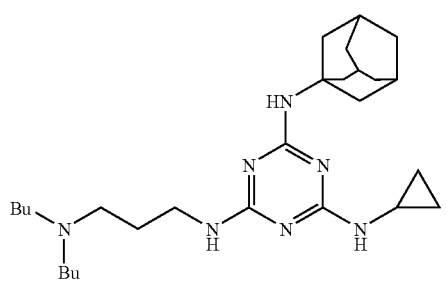

A1

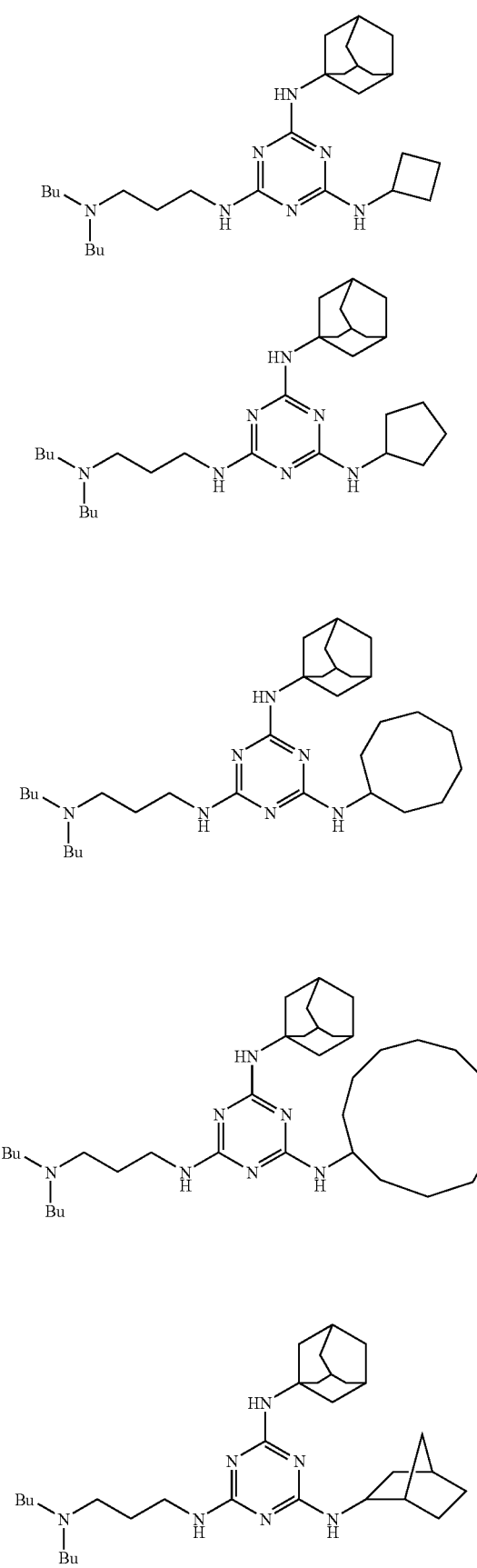
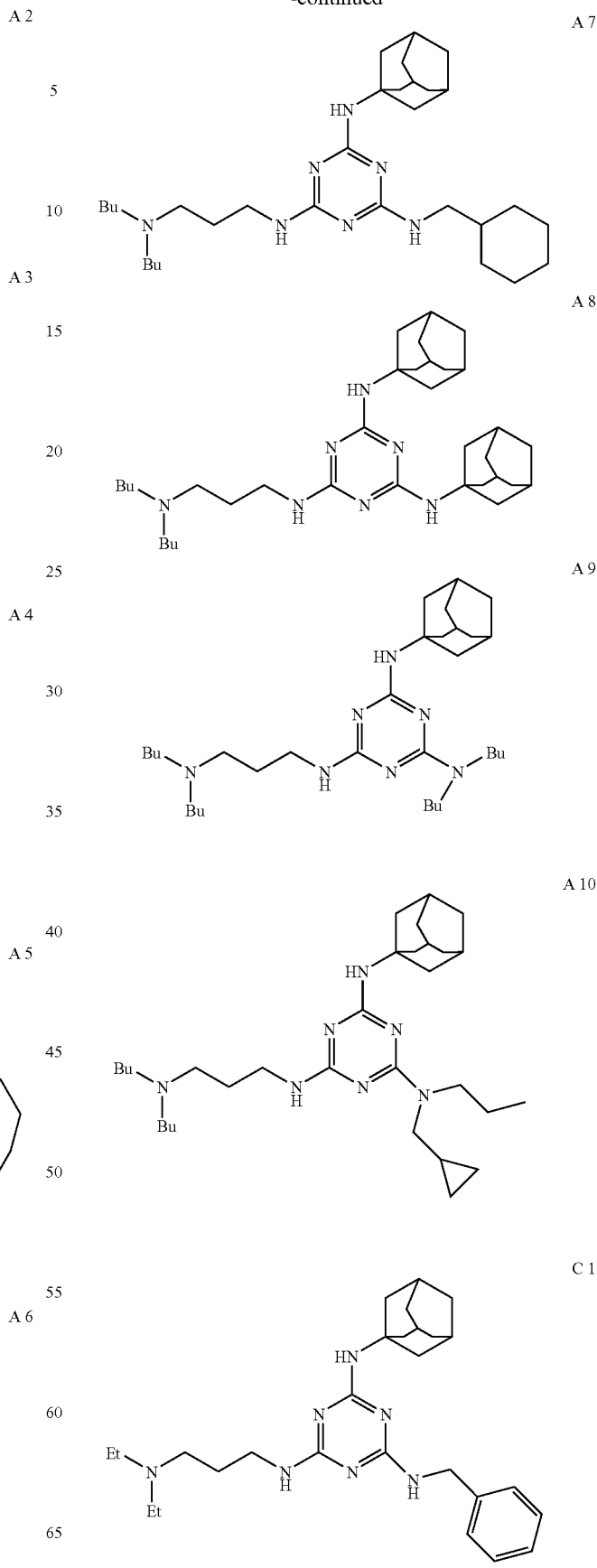

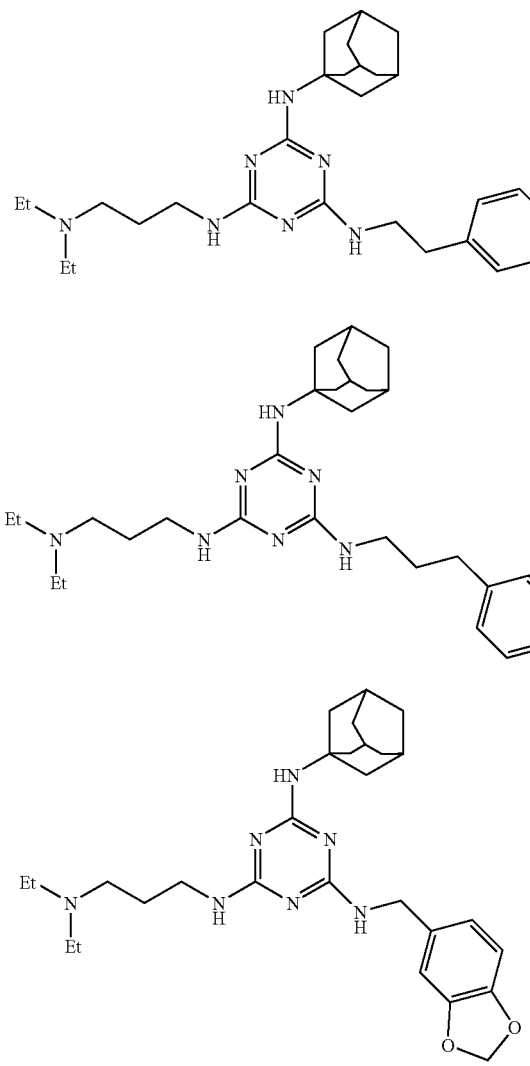
C2
C3
C4
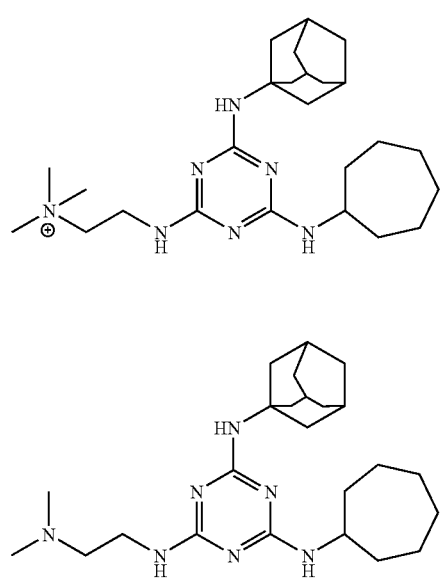
a9
b9
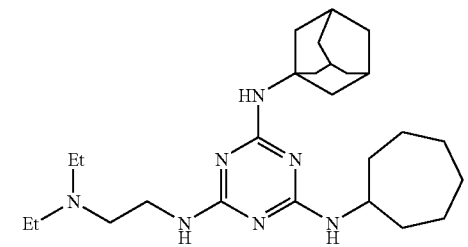
c9
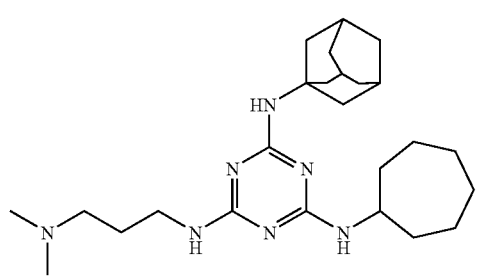
d9
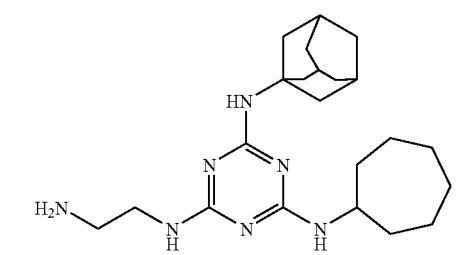
e9
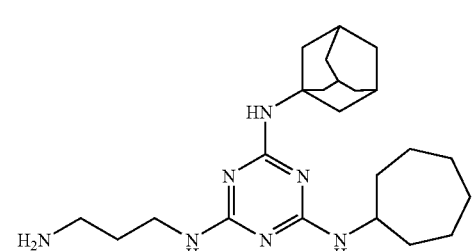
f9
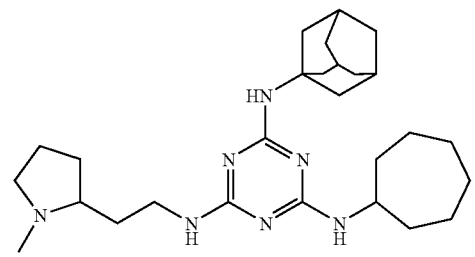
g9
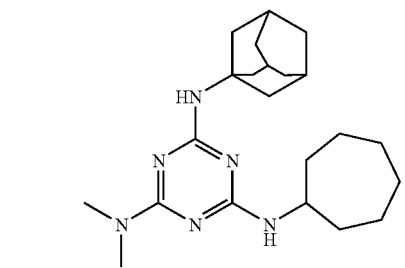
h9

-continued

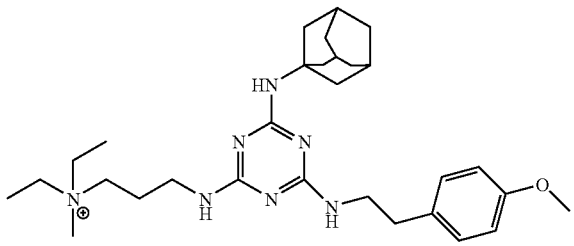

C 5-S

In one embodiment, with respect to compounds of formula II, the compound is:

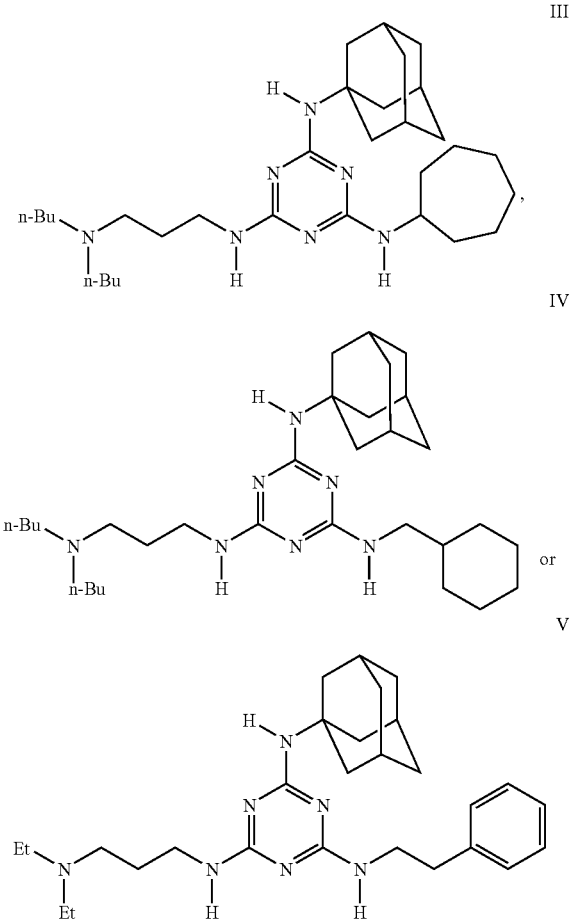

III

IV or

V

In certain aspects and where appropriate, the present invention extends to the preparation of prodrugs and derivatives of the compounds of the invention. Prodrugs are derivatives which have cleavable groups and become by solvolysis or under physiological conditions the compounds of the invention, which are pharmaceutically active, in vivo.

Pharmaceutical Compositions

When employed as pharmaceuticals, the triazine compounds of this invention are typically administered in the form of a pharmaceutical composition. Such compositions can be prepared in a manner well known in the pharmaceutical art and comprise at least one active compound.

Generally, the triazine compounds of this invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds and compositions of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds and compositions of the invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention is dissolved or suspended in a buffered sterile saline injectable aqueous medium to a concentration of approximately 5 mg/mL.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds may be used as therapeutic agents for the treatment of conditions in mammals. Accordingly, the compounds and pharmaceutical compositions of this invention find use as therapeutics for preventing and/or treating infections and like maladies resulting from bacterial, viral or fungal attack, and related conditions in mammals including humans.

In a method of treatment aspect, this invention provides a method of treating a mammal susceptible to or afflicted with a condition associated with or resulting from bacterial, viral or fungal attack or infection, which method comprises administering an effective amount of one or more of the pharmaceutical compositions just described.

In additional method of treatment aspects, this invention provides methods of treating a mammal susceptible to or afflicted with a variety of bacteria or other infections, including strains which have developed resistance to traditional antibiotics, such as, for example, *Staphylococcus aureus*. The method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as viral or microbial conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

The compounds of this invention can be administered as the sole active agent or they can be administered in combination with other agents, including other active derivatives.

General Synthetic Procedures

The compounds of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative s-triazine compounds that have been listed hereinabove. The s-triazine compounds of the invention may be prepared from known or commercially available starting materials and reagents by one skilled in the art of organic synthesis.

With respect to the Figures and Schemes appearing below, it should be understood that reference to $R^2$ pertains to the below Figures and Schemes, and that reference to $R^{2a}$-$R^{2j}$ appearing elsewhere herein, pertains to individual substituents that may be attached to N and positioned, among other places, at the location of R2. Naturally, the placement of $R^{2a}$-$R^{2j}$ may vary within the scope and contemplation of the invention.

General

Unless otherwise noted, materials and solvents were obtained from commercial suppliers and were used without further purification. Anhydrous tetrahydrofuran (THF) and 1-methyl-2-pyrrolidinone (NMP) from Acros were used as reaction solvents without any prior purification. PAL-aldehyde resin from Midwest Bio-Tech was used as the solid support. For the synthesis of building block I, general coupling reactions were performed through solution phase chemistry and were purified by flash column chromatography on Merck silica gel 60-$PF_{245}$. All products were identified by LC/MS from Agilent Technology using a C18 column (20× 4.0 mm), with a gradient of 5-95% $CH_3CN$ (containing 1% acetic acid)-$H_2O$ (containing 1% acetic acid) as eluant.

Equipment

Thermal reactions were performed using a standard heat block from VWR scientific Products using 4 mL vials. Resin filtration procedures were carried out using 70μ PE flit cartridge from Applied Separations.

General schemes for the preparation of Libriaries 1 to 5 are set forth diagrammatically below.

Scheme 1
General synthetic scheme for Libraries 1 and 2.

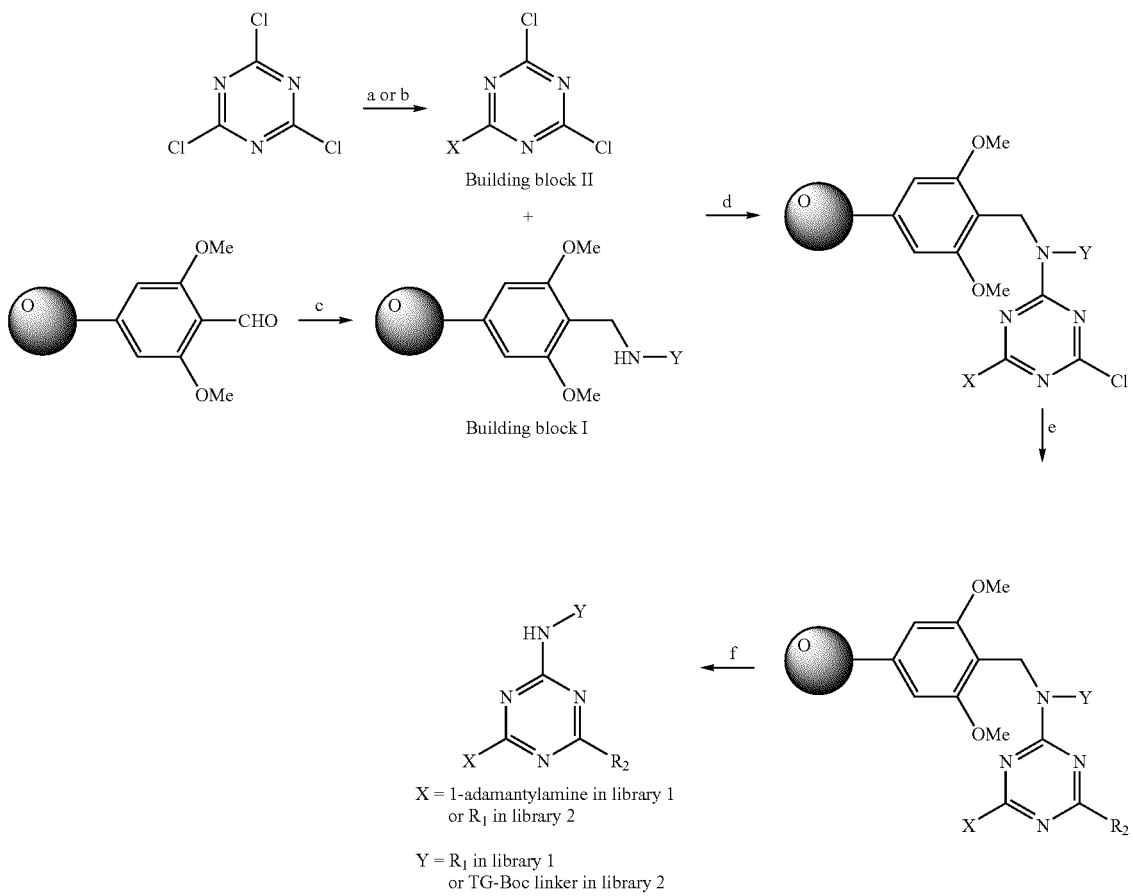

X = 1-adamantylamine in library 1
or $R_1$ in library 2

Y = $R_1$ in library 1
or TG-Boc linker in library 2

(a) 1-adamantylamine, DIEA, THF, room temperature, 1 h; for library 1 (b) $R_1$MgX, THF, 0° C., 2 h; for library 2 (c) $R_1$ amines (for library 1) or TG-Boc linker (1, for library 2), 2% acetic acid in THF, room temperature, 1 h, followed by NaB(OAc)$_3$H, room temperature, 12 h. (d) Building block II in THF, DIEA, 60° C., 1 h (e) $R_2$ amines, DIEA, NMP:n-BuOH = 1:1, 120° C., 3 h. (f) 10% TFA in dichloromethane, room temperature, 1 h.

Scheme 2
General synthetic scheme for Libraries 3, 4 and 5

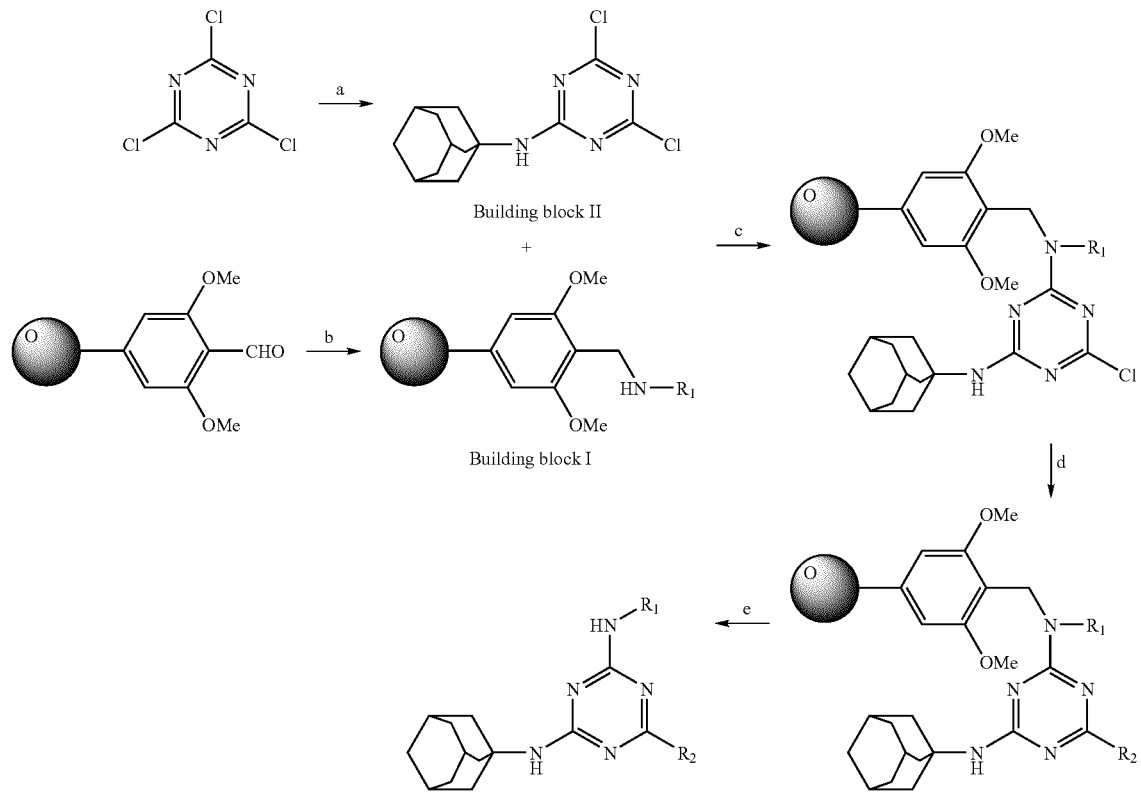

(a) 1-adamantylamine, DIEA, THF, room temperature, 1 h (b) R₁ amines, 2% acetic acid in THF, room temperature, 1 h, followed by NaB(OAc)₃H, room temperature, 12 h. (c) Building block II in THF, DIEA, 60° C., 1 h (d) R₂ amines, DIEA, NMP:n-BuOH = 1:1, 120° C., 3 h. (e) 10% TFA in dichloromethane, room temperature, 1 h.

While the above schemes provide an overview of the synthetic pathways, the following provides the details of these procedures.

Synthesis of Triazine Libraries

Synthesis of the TG-Boc Linker (1) for Library 2

2,2'-(Ethylenedioxy)bis(ethylamine) (10 equiv.) was dissolved in dichloromethane and the solution was cooled down to −78° C. in a dry ice/acetone bath. Di-tert-butyl dicarbonate (1 equiv.) was dissolved in dichloromethane and added to the solution of 2,2'-(Ethylenedioxy)bis(ethylamine) dropwise over a period of 3 h in a nitrogen gas atmosphere. The reaction mixture was allowed to stir for 10 h followed by extraction with saturated NaCl solution. The organic layers were combined and dried over MgSO₄. The solvent was removed in vacuo (70% yield).

General Procedure for Preparing Building Block II via Grignard Alkylation for Library 2

A solution with anhydrous THF (125 mL) of alkylmagnesiumhalide(Br/Cl) (13.0 mmol) was slowly added to a cooled (0° C.-5° C.), mechanically stirred THF solution (125 mL) of cyanuric chloride (10.93 mmol, 2 g); the mixture was stirred at 0° C. for 2 h. The reaction mixture was quenched with 1 N HCl (40 mL). Then the reaction mixture was extracted with ethyl acetate and washed with water. The organic layers were combined and dried over MgSO₄. The solvent was removed in vacuo.

General Procedure for Building Block I Synthesis for Library 1 to 5

2.8 mmole (5 equiv) of R₁ amines (in library 1, 3, 4 and 5) or TG-Boc linker (for library 2).) was added to a suspension of the PAL aldehyde resin (1.3 g, 1.43 mmole) in anhydrous tetrahydrofuran (THF) (50 mL containing 2% of acetic acid) at room temperature. The reaction mixture was shaken for 1 h at room temperature followed by addition of sodium triacetoxyborohydride (2.1 g, 9.9 mmole, 7 equiv.). The reaction mixture was stirred for 12 h and filtered. The resin was washed with N,N-dimethylformamide (DMF) (5 times), alternatively with dichloromethane and methanol (MeOH) (5 times), and finally with dichloromethane (5 times). The resin was dried in vacuo.

Synthesis of Building Blocks II by Solution Phase Synthesis for Library 1, 3, 4 and 5

Cyanuric trichloride (1 equiv.) was dissolved in THF with DIEA (10 equiv.) at 0° C. 1-Adamantylamine (1.2 equiv.) in THF was added dropwise. The reaction mixture was stirred at 0° C. for 1 h. A solid precipitate slowly formed. Upon completion of the reaction, the reaction mixture was quickly filtered through a plug of flash silica and washed with EA. The filtrate was evaporated in vacuo. The resulting products were purified using flash column chromatography (particle size 32-63 µm).

General Procedure for Coupling Building Block I and Building Block II

Building Block II (0.44 mmole) was added to Building Block I (0.11 mmole) in DIEA (1 mL) and anhydrous THF (10 mL) at room temperature. The reaction mixture was heated to 60° C. for 3 h and filtered. The resin was washed with DMF (5 times), alternatively with dichloromethane and methanol (5 times), and finally dichloromethane (5 times). The resin was dried in vacuo.

General Procedure for the Final Amination on the Resin and Product Cleavage Reaction.

The desired amines (4 equiv.) were added to the resin (10 mg), coupled with Building Block I and Building Block II, in DIEA (8 µL) and 1 mL of NMP: n-BuOH (1:1). The reaction mixture was heated to 120° C. for 3 h. The resin was washed with DMF (5 times), alternatively with dichloromethane and methanol (5 times), and finally dichloromethane (5 times). The resin was dried in vacuo. The product cleavage reaction was performed using 10% trifluoroacetic acid (TFA) in dichloromethane (1 mL) for 30 min at room temperature and washed with dichloromethane (0.5 mL). Free hydroxyl containing compounds were further treated with a piperazine resin in 0.5 mL THF at room temperature for 5 h to cleave the trifluoroacetic ester that was formed upon treatment with TFA. The resin was filtered out and washed with 0.1 mL THF. The purity and identity of all the products were monitored by LC-MS at 250 nm (Agilent Model 1100) and more than 90% of the compounds demonstrated >90% purity.

The first two libraries were created in order to screen various functional groups for their antimicrobial activity. Two mono-substituted triazine templates were used for these libraries, where amantadine and 2,2'-(Ethylenedioxy)bis (ethylamine) were prefixed onto the triazine scaffold (FIG. 1). Amantadine was used to represent one hydrophobic group, and 2,2'-(Ethylenedioxy)bis(ethylamine) was used to represent one charged group.

In addition of the prefixed group, the series of compounds were made to bring in two more groups (hydrophobic, bulky, positively charged, etc) to positions $R^1$ and $R^2$, respectively. A total of 80 compounds in Library 1 and 72 compounds in Library 2 were synthesized utilizing an orthogonal synthetic approach based on a triazine scaffold (Scheme 1) and their antimicrobial activities were tested against gram-positive bacteria *B. Subtilis*. The subsequent Libraries 3 and 4 were designed based on the results from libraries 1 and 2 (FIG. 2 and Scheme 2), and Library 5 was made to further optimize the $R^1$ and $R^2$ groups of the most promising compounds from previous design (FIG. 3 and Scheme 2).

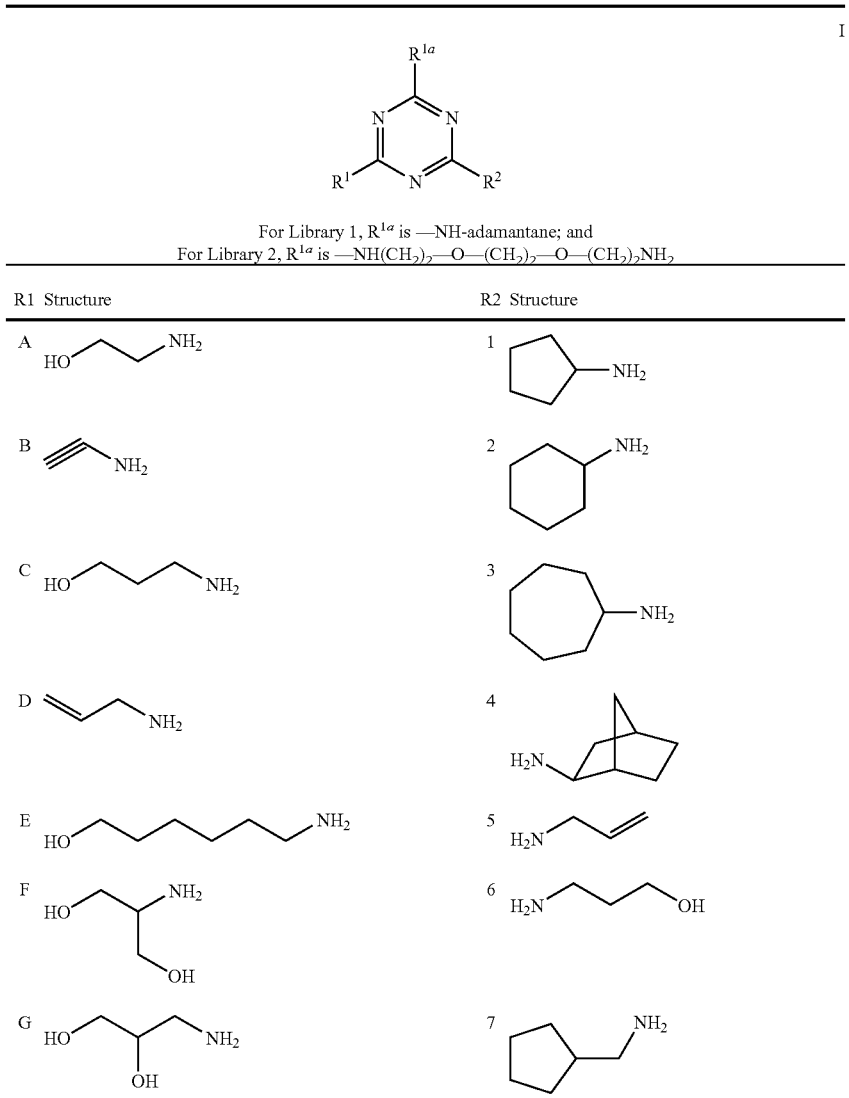

For Library 1, $R^{1a}$ is —NH-adamantane; and
For Library 2, $R^{1a}$ is —NH(CH$_2$)$_2$—O—(CH$_2$)$_2$—O—(CH$_2$)$_2$NH$_2$ -continued
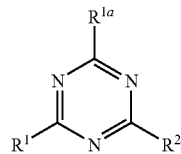
For Library 1, $R^{1a}$ is —NH-adamantane; and
For Library 2, $R^{1a}$ is —NH(CH$_2$)$_2$—O—(CH$_2$)$_2$—O—(CH$_2$)$_2$NH$_2$
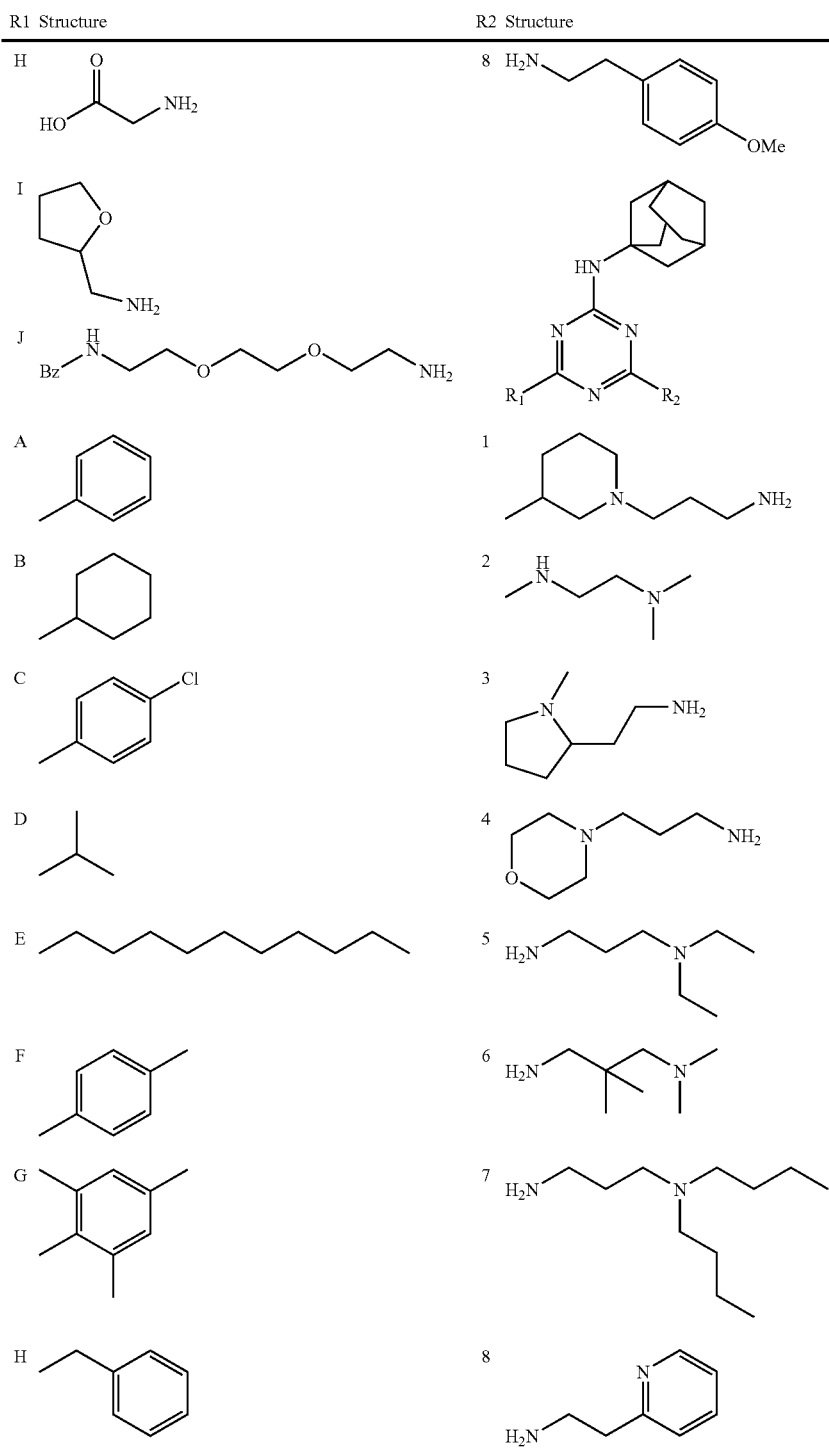

-continued
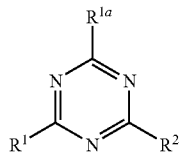
I
For Library 1, R$^{1a}$ is —NH-adamantane; and
For Library 2, R$^{1a}$ is —NH(CH$_2$)$_2$—O—(CH$_2$)$_2$—O—(CH$_2$)$_2$NH$_2$
| R1 Structure | R2 Structure | |
|---|---|---|
| 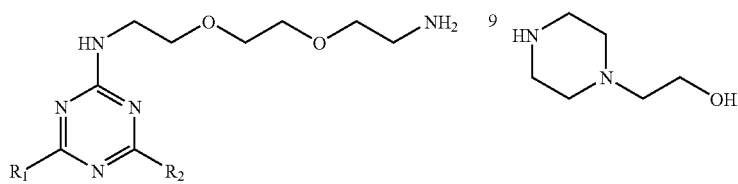 | | 9 |
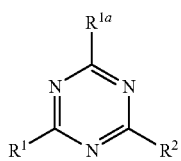
I
For Library 3, R$^{1a}$ is —NH-adamantane; and
For Library 4, R$^{1a}$ is —NH-adamantane;
and R$^2$ is —NH(CH$_2$)$_2$—O—(CH$_2$)$_2$—O—(CH$_2$)$_2$NH$_2$
| R1 Structure | | R2 Structure | |
|---|---|---|---|
| A | | A | |
| B | | B | |
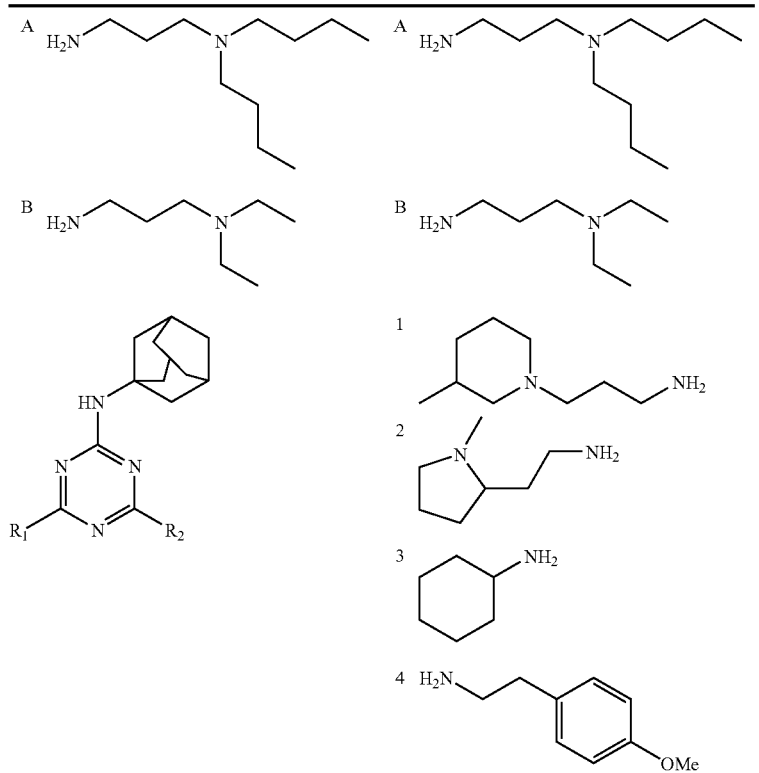

-continued
| | |
|---|---|
| 5 | 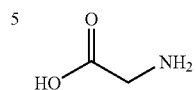 |
| 6 | 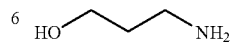 |
| 7 | 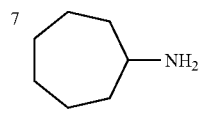 |
| | R1 Structure | |
|---|---|---|
| 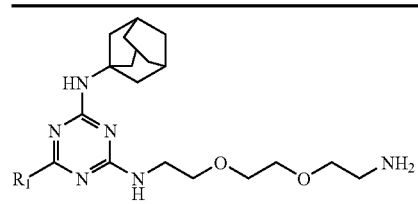 | 1 |  |
| | 2 | 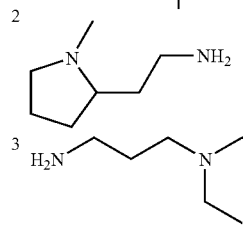 |
| | 3 | 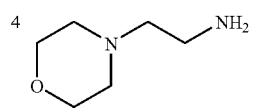 |
| | 4 | 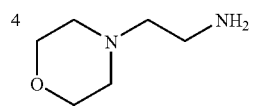 |
| | 5 | 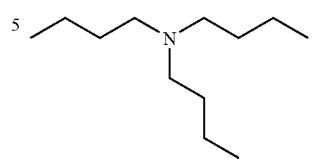 |
| | 6 | 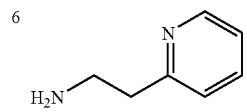 |
| | 7 | 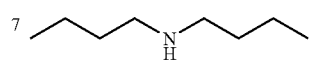 |
| | 8 | 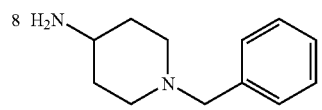 |
| | 9 | 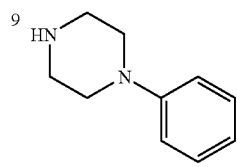 |
| | 10 | 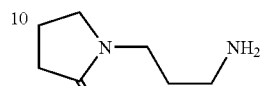 |
| | 11 | 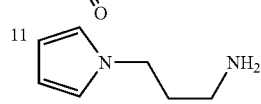 |

EXAMPLES

The following examples are presented in order to more fully illustrate the preferred embodiments of the invention. They should in no way be construed, however, as limiting the broad scope of the invention.

Example 1

Antibacterial Testing

The antimicrobial activity of each triazine compound was tested by following standard broth microdilution protocols recommended by the National Committee for Clinical Laboratory Standard. All compounds were initially tested against *Bacillus subtilis* (ATCC 6633; Rockville, Md.). The three compounds showing the most antimicrobial activity against *Bacillus subtilis*, A7 (Library 3), A4 (Library 5) and C2 (Library 5), were further tested against ampicillin- and streptomycin-resistant strain *E. coli* (D31; *E. coli* Genetic Resource Center, Yale University, New Haven, Conn.), multi-drug resistant strain *S. aureus* (ATCC BAA-44), *Acinetobacter baumannii* (ATCC BAA-747), and *Enterococcus faecalis* (ATCC 29212). Bacteria were grown in Mueller Hinton Broth (MHB) at 37° C. for overnight. Then, cultures were diluted in MHB to a final concentration of $2 \times 10^4$ to $2 \times 10^5$ CFU/mL. Bacterial inocula were incubated at 37° C. in PBS buffer (pH 7.2) with varying concentrations of 2-fold dilution of triazine stocks. The 18-hour absorbance data were used to calculate the percent inhibition for each sample by comparing with the absorbance of cultures without triazine compounds. Bacterial growth was measured by turbidity as optical density at 600 nm using a Genesys 5 Spectrophotometer (Rochester, N.Y.). The concentration of peptide that resulted in 50% was recorded as $MIC_{50}$.

Example 2

Hemolytic Activity

Hemolytic activity of three triazine compounds (A7 from library 3, A4 and C2 from library 5) was assessed on fresh sheep erythrocytes (Fitzgerald Inc., Concord, Mass.). The red blood cell suspension was incubated in PBS buffer (pH 7.2) with varying concentrations of sample stocks at 37° C. for 30 minutes, and then spun down at 3,000 rpm for 10 mins. The resulting supernatant was diluted by a factor of 40 in distilled water. The absorbance of the supernatant at 540 nm was measured using a Genesys 5 Spectrophotometer. Zero hemolysis and 100% hemolysis controls were obtained by incubating the cells with buffer and 1% Triton-X, respectively. Sample concentration yielding 50% hemolysis was used as hemolytic dose ($HD_{50}$) determined from dose-response curves.

Results

The initial screening of two groups of mono-substituted 1,3,5-triazine compounds (Libraries 1 & 2) against gram-positive bacteria *B. subtilis* at 100 uM concentration revealed 30 antimicrobial active compounds. However, none of these compounds showed antimicrobial activity at lower concentration (50 uM). In order to improve the activity, the $R^1$ and $R^2$ side chains in each of the 30 compounds were organized and tables of frequency of effectiveness from Libraries 1 and 2 were made (Tables 1 and 2). From these tables, most effective side chains from the two libraries were identified, and were then used to design Libraries 3 and 4. Due to synthesis difficulties with some of the compounds, only limited combinations of these groups were synthesized.

TABLE 1

Frequency of effectiveness from library 1 (active against B. sub. at 100 uM;: B2, C2, F2, H2, F3, G3, H3, E6, C7, H7, C8, F8 G8).

Structure I: 1,3,5-triazine with $R^{1a}$, $R^1$, $R^2$ substituents; $R^{1a}$ = NH-adamantane

| R1 | Structure | Freq. |
|---|---|---|
| A | HO-CH₂CH₂-NH₂ | 0 |
| B | CH₂=CH-NH₂ | 1 |
| C | HO-(CH₂)₃-NH₂ | 3 |
| D | CH₂=CH-CH₂-NH₂ | 0 |
| E | HO-(CH₂)₆-NH₂ | 1 |
| F | HO-CH₂-CH(NH₂)-CH₂-OH | 3 |
| G | HO-CH₂-CH(OH)-CH₂-NH₂ | 2 |
| H | HO-C(=O)-CH₂-NH₂ | 3 |
| I | tetrahydrofuran-2-yl-CH₂-NH₂ | 0 |
| J | Bz-NH-CH₂CH₂-O-CH₂CH₂-O-CH₂CH₂-NH₂ | 0 |

| R2 | Structure | Freq. |
|---|---|---|
| 1 | cyclopentyl-NH₂ | 0 |
| 2 | cyclohexyl-NH₂ | 4 |
| 3 | cycloheptyl-NH₂ | 3 |

TABLE 1-continued

| | | |
|---|---|---|
| 4 | 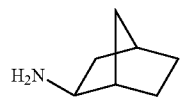 | 0 |
| 5 | 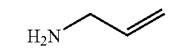 | 0 |
| 6 | 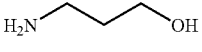 | 1 |
| 7 | 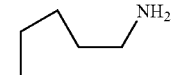 | 2 |
| 8 | 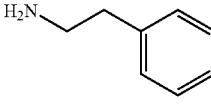 | 3 |

TABLE 2

Frequency of effectiveness from library 2 (active against B. sub. at 100 uM: B1, C1, E1, F1, C3, E3, F3, C5, E5, F5, E6,; A7, B7, C7, E7, F7, H7).

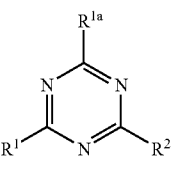

$R^{1a}$ = NH(CH$_2$)$_2$—O—(CH$_2$)$_2$—O—(CH$_2$)$_2$NH$_2$

| R1 | Structure | Freq. |
|---|---|---|
| A | 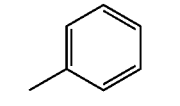 | 1 |
| B | 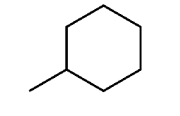 | 2 |
| C | 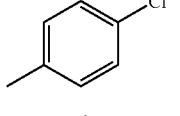 | 4 |
| D | 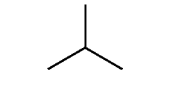 | 0 |
| E | 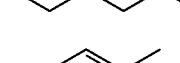 | 5 |
| F | 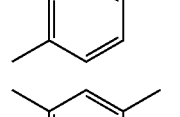 | 4 |
| G | 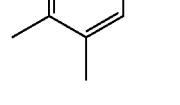 | 0 |

TABLE 2-continued

| | | |
|---|---|---|
| H | 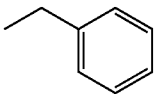 | 1 |

| R2 | Structure | Freq. |
|---|---|---|
| 1 | 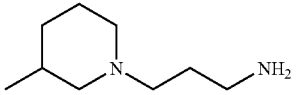 | 4 |
| 2 | 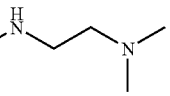 | 0 |
| 3 | 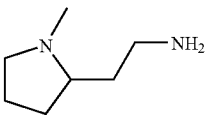 | 3 |
| 4 | 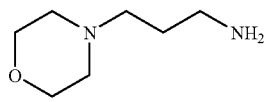 | 0 |
| 5 | 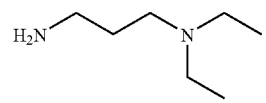 | 3 |
| 6 | 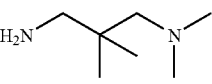 | 1 |
| 7 | 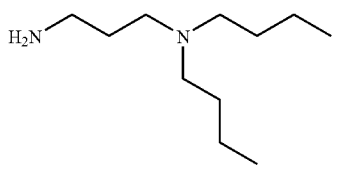 | 6 |
| 8 | 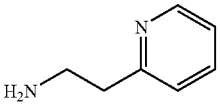 | 0 |
| 9 | 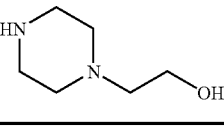 | 0 |

The screening of compounds in Libraries 3 & 4 against Gram-positive bacteria *B. subtilis* further revealed 11 compounds that had improved antimicrobial activities, and their hemolytic activities (Table 3). Among these compounds, A7 and B4 from Library 3 were selected as the templates for designing Library 5. Various length, charge, or bulkiness were tested in Library 5 in order to optimize the compounds, as well as to gain further insight as to the structure-function relationship of these peptide mimics.

TABLE 3

Successful screening results from library 3 & 4

| Compound | MIC50 (uM) | Hemolysis (at 100 uM) |
|---|---|---|
| AA | 7.5 | <10% |
| AB | 7.5 | <10% |
| A1 | 7.5 | <10% |
| A3 | 7.5 | <10% |
| A4 | 7.5 | <10% |
| A7 | 2.5 | <10% |
| B4 | 2.5 | <10% |
| B7 | 7.5 | <10% |
| 7 | 7.5 | 50% |
| 8 | 17.5 | <10% |
| 9 | 17.5 | <10% |

The antimicrobial test results for the Library 5 compounds showed some interesting trends and various degrees of activities against *B. subtilis* (Table 4). In general, increasing in bulkiness (ring size) on one side chain of triazine compounds increased the antimicrobial activity, where size 7 and 8 seemed to be optimal. If the ring size was increased to 12 (A5), activity decreased almost 8-fold comparing to size 7 or 8 compounds. Interestingly, triazine compounds with two amantadine groups had much less antimicrobial activity compared with compounds having only one amantadine group. On the other hand, increasing the amine chain length did not show obvious trend, with some slight increase in activity among some compounds. In addition, quaternary ammonium cation also did not have any large effect on improving the activity.

TABLE 4

MIC50 results from library 5.

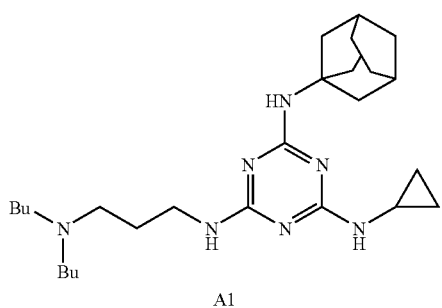

A1

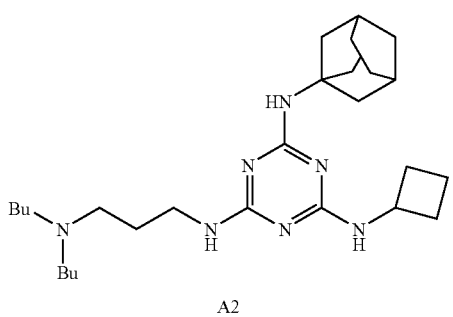

A2

TABLE 4-continued

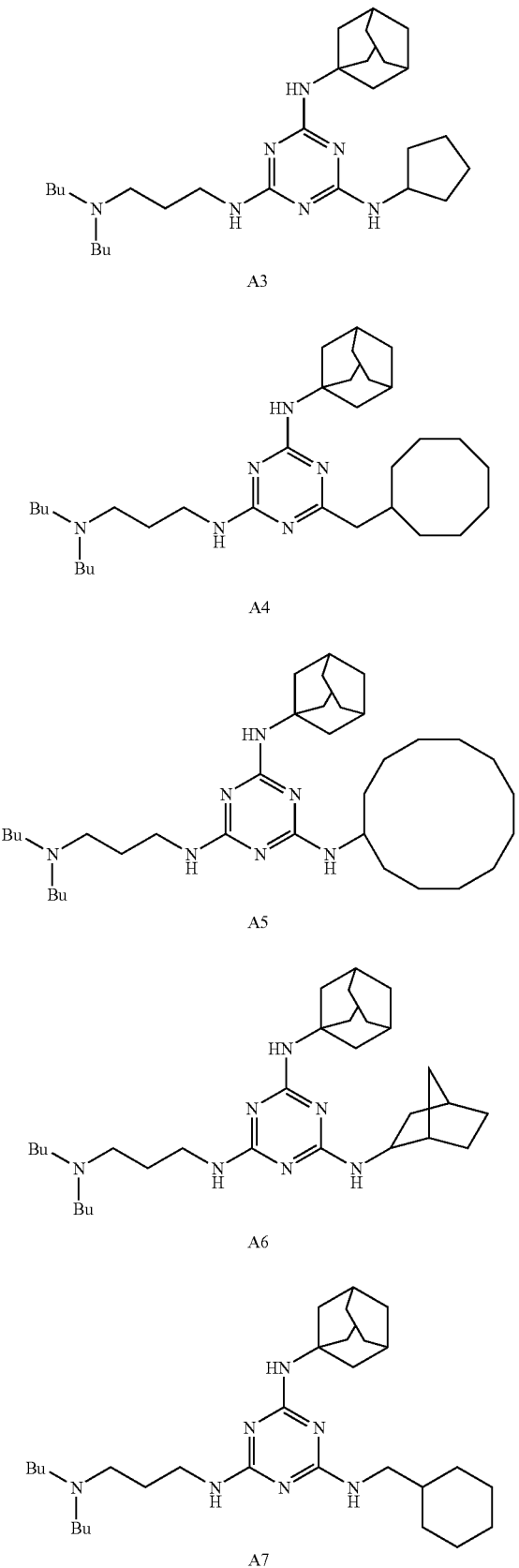

TABLE 4-continued
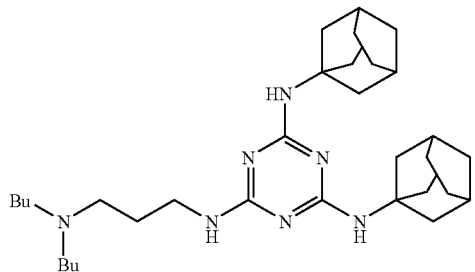
A8
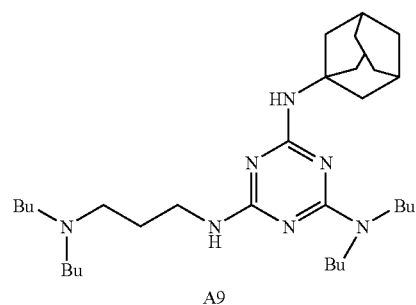
A9
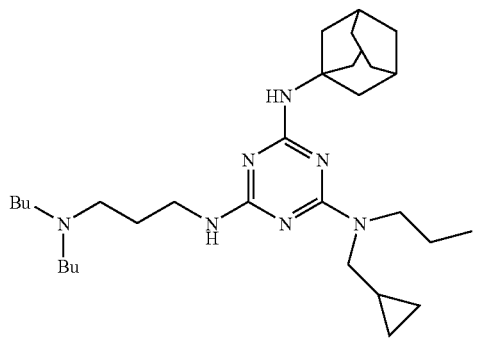
A10
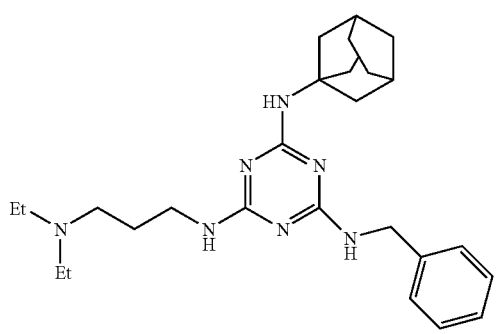
C1
TABLE 4-continued
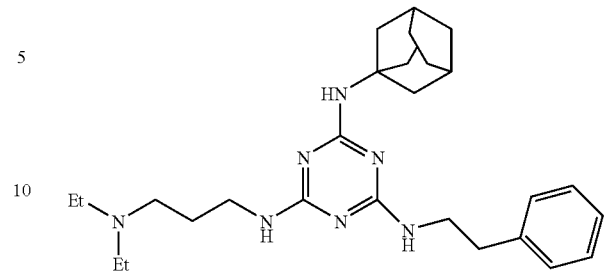
C2
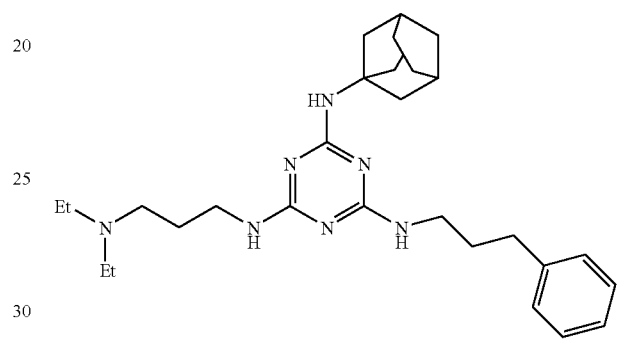
C3
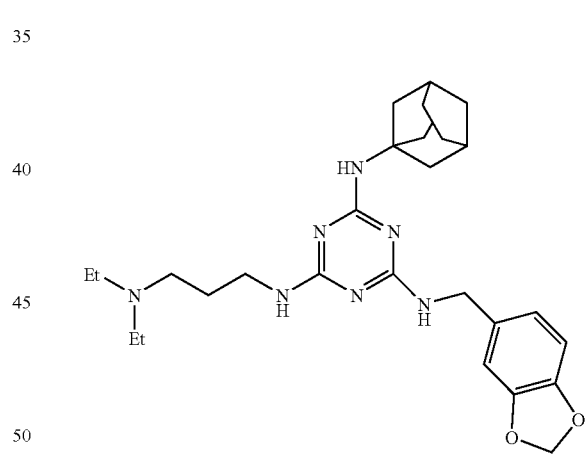
C4
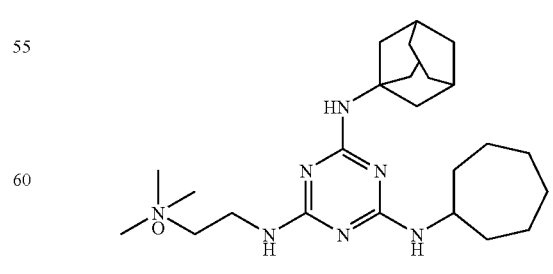
a9

TABLE 4-continued

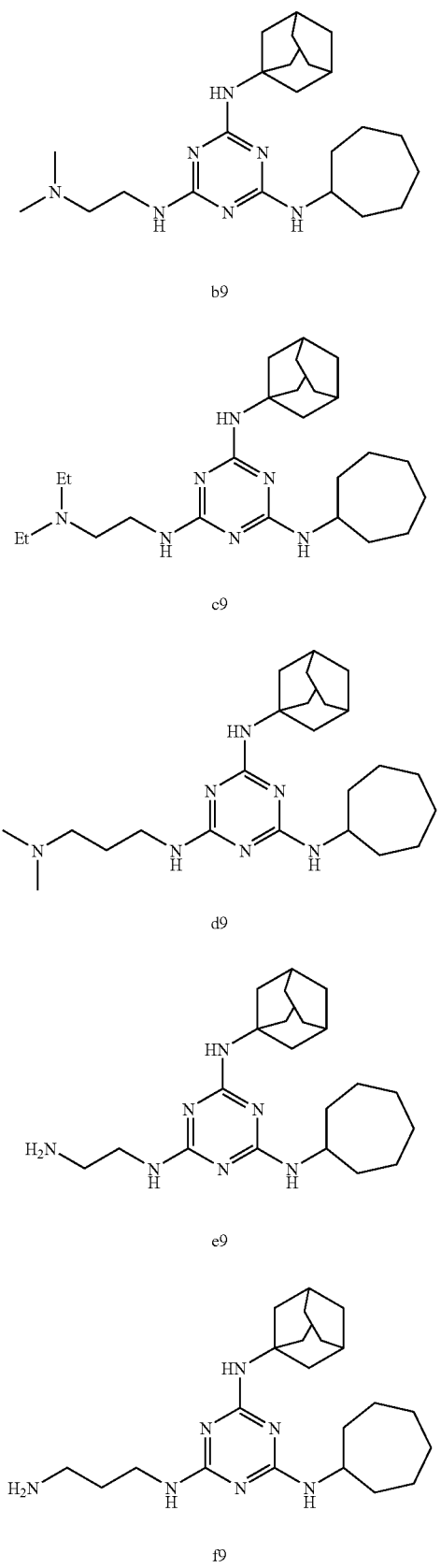

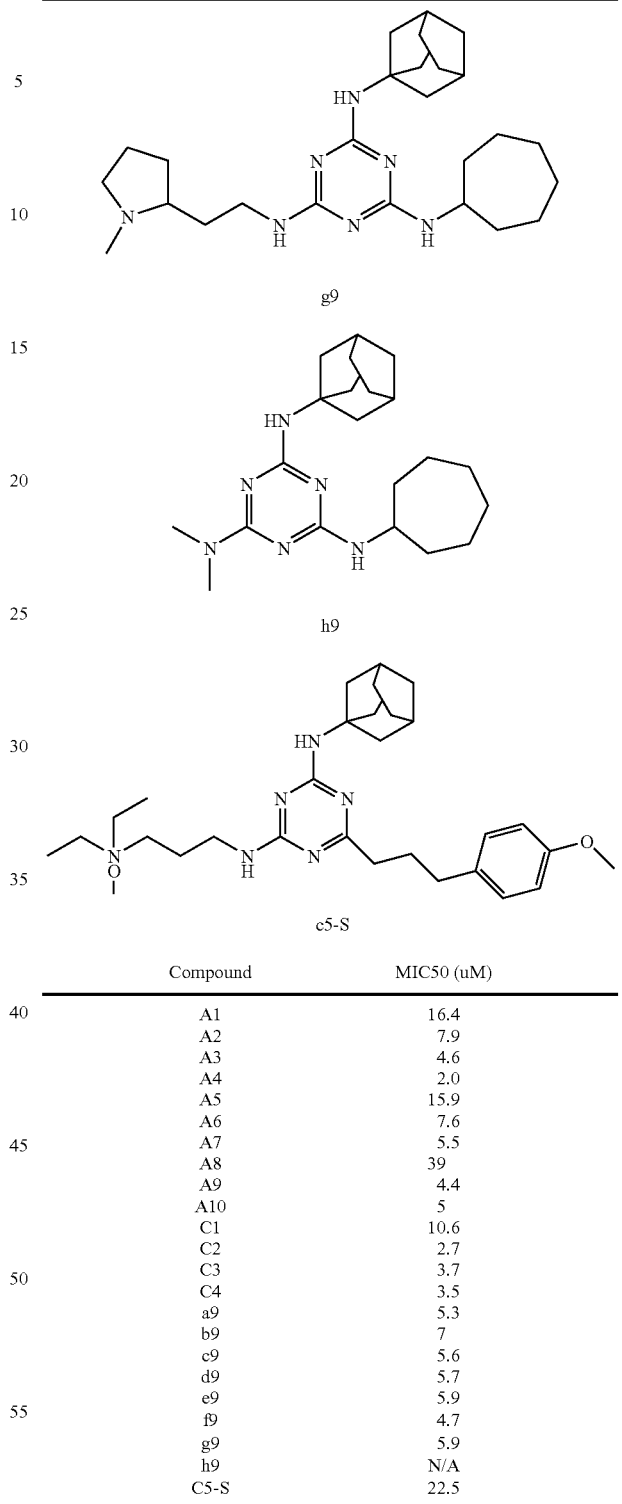

| Compound | MIC50 (uM) |
|---|---|
| A1 | 16.4 |
| A2 | 7.9 |
| A3 | 4.6 |
| A4 | 2.0 |
| A5 | 15.9 |
| A6 | 7.6 |
| A7 | 5.5 |
| A8 | 39 |
| A9 | 4.4 |
| A10 | 5 |
| C1 | 10.6 |
| C2 | 2.7 |
| C3 | 3.7 |
| C4 | 3.5 |
| a9 | 5.3 |
| b9 | 7 |
| c9 | 5.6 |
| d9 | 5.7 |
| e9 | 5.9 |
| f9 | 4.7 |
| g9 | 5.9 |
| h9 | N/A |
| C5-S | 22.5 |

Finally, three compounds, A7 from Library 3, A4 and C2 from Library 5, were selected and their antimicrobial activity and hemolytic activity were tested against different bacteria, and sheep blood cells (Table 5). The results showed that these compounds were generally more selective against gram-positive bacteria, and were not highly hemolytic even at high concentration.

TABLE 5

MIC50 and HC50 of compounds A4 (from library 5),
C2 (from library 5) and A7 (from library 3) against different
bacteria and sheep blood cells.

|  | MIC50 (uM) A4 | MIC50 (uM) C2 | MIC50 (uM) A7 |
| --- | --- | --- | --- |
| A. baumannii | 84 | 22 | 53 |
| B. anthracis | 86 | 21 | 41 |
| E. coli D31 | 546 | 200 | 618 |
| E. faecalis | 320 | 142 | 266 |
| S. aureus | 70 | 17 | 68 |
|  | HC50 A4 | HC50 C2 | HC50 A7 |
| Hemolysis | >>2 mg/ml | >>2 mg/ml | >>2 mg/ml |

Example 3

Calcein Dye Leakage

To test whether the active triazine compounds kill bacteria via disrupting membrane integrity, a calcein dye leakage experiment was carried out with compound C2 with ampicillin and one of the triazine compounds with little antimicrobial activity (h-9) as control. The method of preparation of dye-encapsulated vesicles has been reported in detail. Lasch, V.; Weissig, M. *Brandl in Liposomes: a Practical Approach* Eds.: Taylor, K. M. G.; Craig, D.Q.M. Oxford University Press, Oxford, 2003; pp. 10-12. The results are graphically presented in FIG. 1, which presents the results of calcein leakage induced by 1% Triton, C2 (50 µM), h9 (90 µM) and ampicillin (70 µM). The fraction of leakage was calculated from the fluorescence intensity at 515 nm, with 100% leakage calibrated by addition of 1% Triton X-100.

From the results, C2 was found to cause 100% dye leakage at 50 µM. The results confirmed that the antimicrobial active triazine compound could cause dye leakage from negatively charged 1-palmitoyl-2-oleoyl-sn-glycero-3-[phospho-rac-(1-glycerol)] (POPG) lipid vesicles, while neither ampicillin nor compound C2 caused dye leakage.

REFERENCES

1. Zasloff, M. 2002. Antimicrobial peptides of multicellular organisms. *Nature* 415(6870):389-95.
2. Boman, H. G. 2003. Antibacterial peptides: basic facts and emerging concepts. *J. Intern. Med.* 254(3):197-215.
3. Medzhitov, R. and C. Janeway, Jr. 2000. Innate immune recognition: mechanisms and pathways. *Immunol. Rev.* 173:89-97.
4. Brogden, K. A., Ackermann, M., McCray, P. B., and Tack, B. F. 2003. Antimicrobial peptides in animals and their role in host defences. *Int J Antimicrob Agents* 22(5):465-78.
5. Hancock, R. E. 1999. Host defence (cationic) peptides: what is their future clinical potential? *Drugs* 57(4):469-73.
6. Fischetti, V. A. 2003. Novel method to control pathogenic bacteria on human mucous membranes. *Ann. N.Y. Acad. Sci.* 987:207-14.
7. Yeaman, M. R. and Yount, N.Y. 2003. Mechanisms of antimicrobial peptide action and resistance. *Pharmacol Rev.* 55:27-55.
8. Strçm, M. B., Haug, B. E., Skar, M. L., Stensen, W., Stiberg, T. and Svendsen, J. S. 2003. The pharmacophore of short cationic antibacterial peptides. *J. Med. Chem.* 46(9):1567-1570.
9. Liu, Z., Brady, A., Young, A., Rasimick, B., Chen, K., Zhou, C. and Kallenbach, N. R. 2007. Length effects in antimicrobial peptides of the (RW)n Series. *Antimicrobial Agents and Chemotherapy* 51 (2):597-603.
10. Arvidsson, P. I., Frackenpohl, J., Ryder, N. S., Leichty, B., Petersen, F., Zimmermann, H., Camenisch, G. P., Woessner, R. and Seebach, D. 2001. On the antimicrobial and hemolytic activities of amphiphilic β-peptides. *ChemBioChem* 2(10):771-773.
11. Goodson, B., Ehrhardt, A., Ng, S., Nuss, J., Johnson, K., Giedlin, M., Yamamoto, R., Moos, W. H., Krebber, A., Ladner, M., Giacona, M. B., Vitt, C. and Winter, J. 1999. Characterization of novel antimicrobial peptoids. *Antimicrobial Agents and Chemotherapy* 43(6):1429-1434.
12. Rennie, J., Amt, L., Tang, H., Nuesslein, K. and Tew, G. N. 2005. Simple oligomers as antimicrobial peptide mimics. *J. Industrial Microbiology & Biotech.* 32(7):296-300.
13. Silen, J. L., Lu, A. T., Solas, D. W., Gore, M. A., Maclean, D., Shah, N. H., Coffin, J. M., Bhinderwala, N. S., Wang, Y., Tsutsui, K. T., Look, G. C., Campbell, D. A., Hale, R. L., Navre, M. and DeLuca-Flaherty, C. R. 1998. Screening for novel antimicrobials from encoded combinatorial libraries by using a two-dimensional agar format. *Antimicrobial Agents and Chemotherapy* 42(6): 1447-1453.
14. Giacometti, A., Cirioni, O., Greganti, G., Quarta, M. and Scalise, G. 1998. In vitro activities of membrane-active peptides against gram-positive and gram-negative aerobic bacteria. *Antimicrobial Agents and Chemotherapy* 42(12): 3320-3324.
15. Giacometti, A., Cirioni, O., Barchiesi, F., Del Prete, M. S, and Scalise, G. 1999. Antimicrobial activity of polycationic peptides. *Peptides* 20(11):1265-1273.
16. Huang, H. W. 2000. Action of antimicrobial peptides: two-state model. *Biochemistry* 39(29):8347-8352.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for nucleic acids or polys-triazine compounds are approximate, and are provided for description.

All publications, including but not limited to patents and patent applications, cited in this specification are herein incorporated by reference as if each individual publication were specifically and individually indicated to be incorporated by reference herein as though fully set forth.

What is claimed is:

1. A s-triazine compound having a formula II:

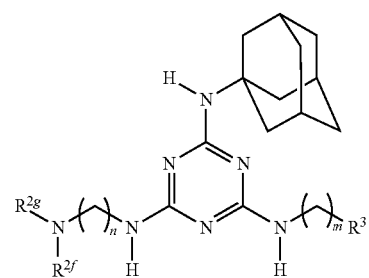

II wherein each of $R^{2f}$, and $R^{2g}$ is independently selected from hydrogen, and substituted or unsubstituted $C_1$-$C_6$ alkyl; or $R^{2f}$ and $R^{2g}$ may join together to form a cycloheteroalkyl ring of 3-7 atoms; m is 0, 1, 2, or 3; and n is 2, 3, or 4; and $R^3$ is selected from 3-13 membered cycloalkyl ring;

or a pharmaceutically acceptable salt thereof;

and stereoisomers, isotopic variants and tautomers thereof.

2. A compound of claim 1 wherein $R^3$ is cyclopropyl or cyclobutyl.

3. A compound of claim 1 wherein $R^3$ is cycloheptyl.

4. A s-triazine compound having a formula II:

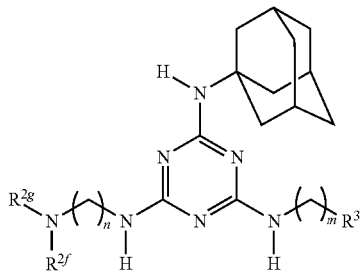

wherein each of $R^{2f}$, and $R^{2g}$ is independently selected from hydrogen, and substituted or unsubstituted $C_1$-$C_6$ alkyl; or $R^{2f}$ and $R^{2g}$ may join together to form a cycloheteroalkyl ring of 3-7 atoms; m is 0, 1, 2, or 3; and n is 2, 3, or 4; and $R^3$ is $R^4$; and $R^4$ is selected from substituted or unsubstituted

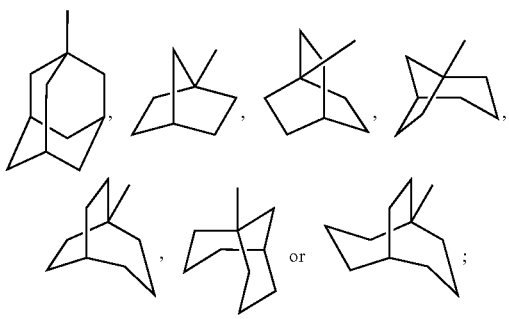

or a pharmaceutically acceptable salt thereof;

and stereoisomers, isotopic variants and tautomers thereof.

5. A s-triazine compound having a formula II:

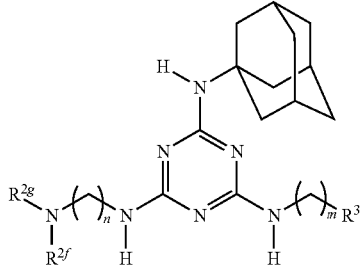

wherein each of $R^{2f}$, and $R^{2g}$ g is independently selected from hydrogen, and substituted or unsubstituted $C_1$-$C_6$ alkyl;

or $R^{2f}$ and $R^{2g}$ may join together to form a cycloheteroalkyl ring of 3-7 atoms; m is 0, 1, 2, or 3; and n is 2, 3, or 4;

and $R^3$ is $C_1$-$C_6$ alkyl, unsubsituted or substituted with acyl, acylamino, acyloxy, alkoxy, alkoxycarbonyl, alkoxycarbonylamino, amino, azido, cyano, halogen, hydroxyl, heteroaryl, keto, nitro, thioalkoxy, alkyl-S(O)—, aryl-S(O)—, alkyl-S(O)$_2$—, or aryl-S(O)$_2$—;

or a pharmaceutically acceptable salt thereof;

and stereoisomers, isotopic variants and tautomers thereof.

6. A s-triazine compound having a formula II:

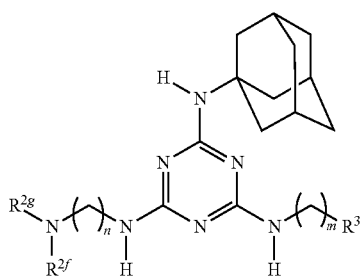

wherein each of $R^{2f}$, and $R^{2g}$ is independently selected from hydrogen, and substituted or unsubstituted $C_1$-$C_6$ alkyl; or $R^{2f}$ and $R^{2g}$ may join together to form a cycloheteroalkyl ring of 3-7 atoms; m is 0, 1, 2, or 3; and n is 2, 3, or 4;

and $R^3$ is unsubstituted phenyl;

or a pharmaceutically acceptable salt thereof;

and stereoisomers, isotopic variants and tautomers thereof.

7. A compound selected from:

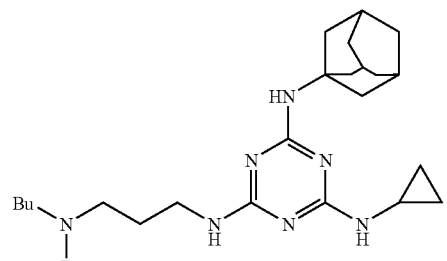

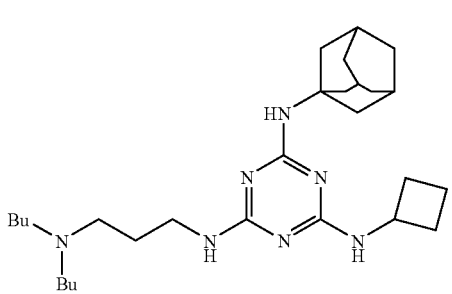

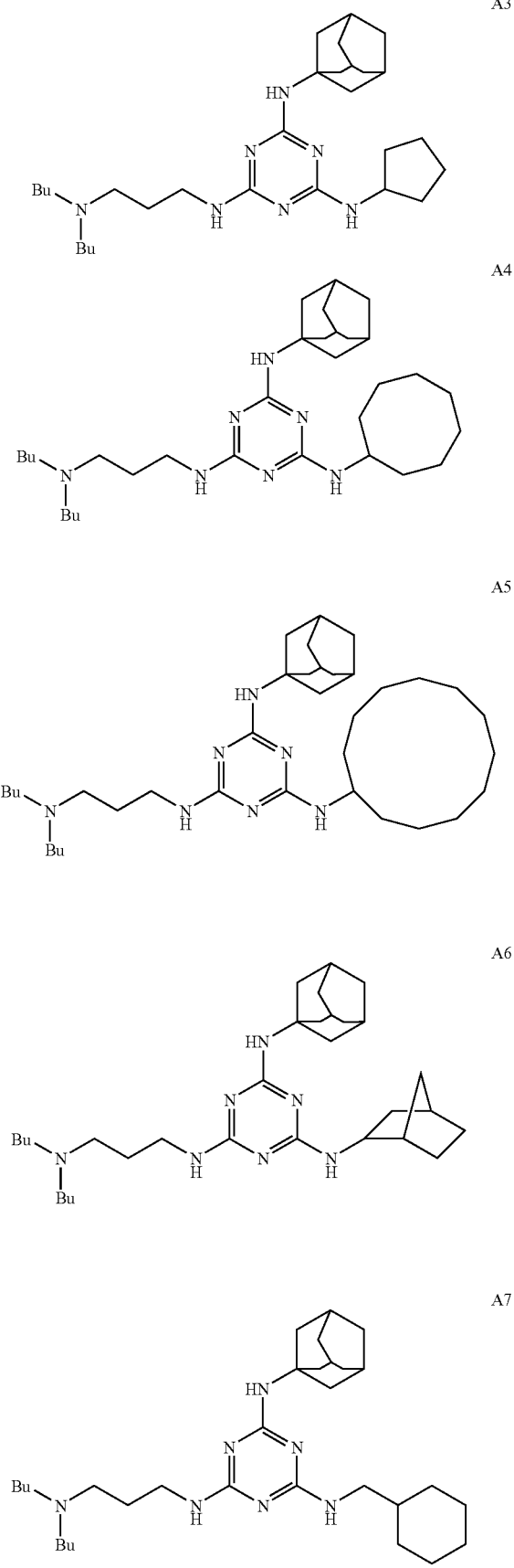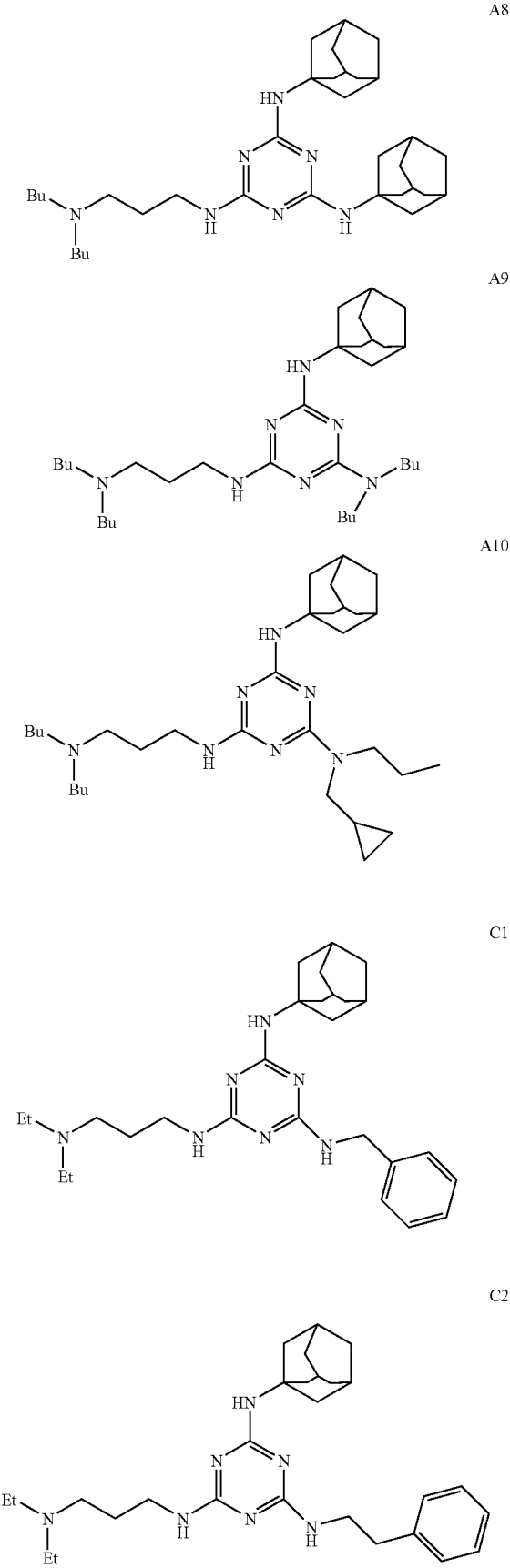

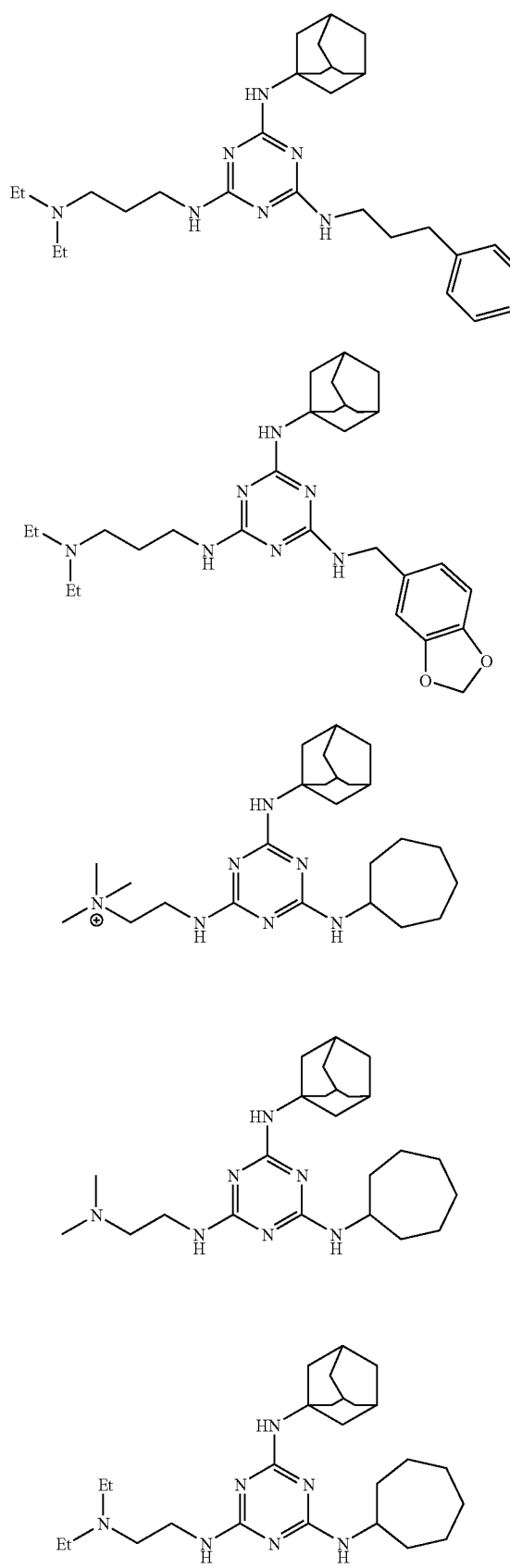
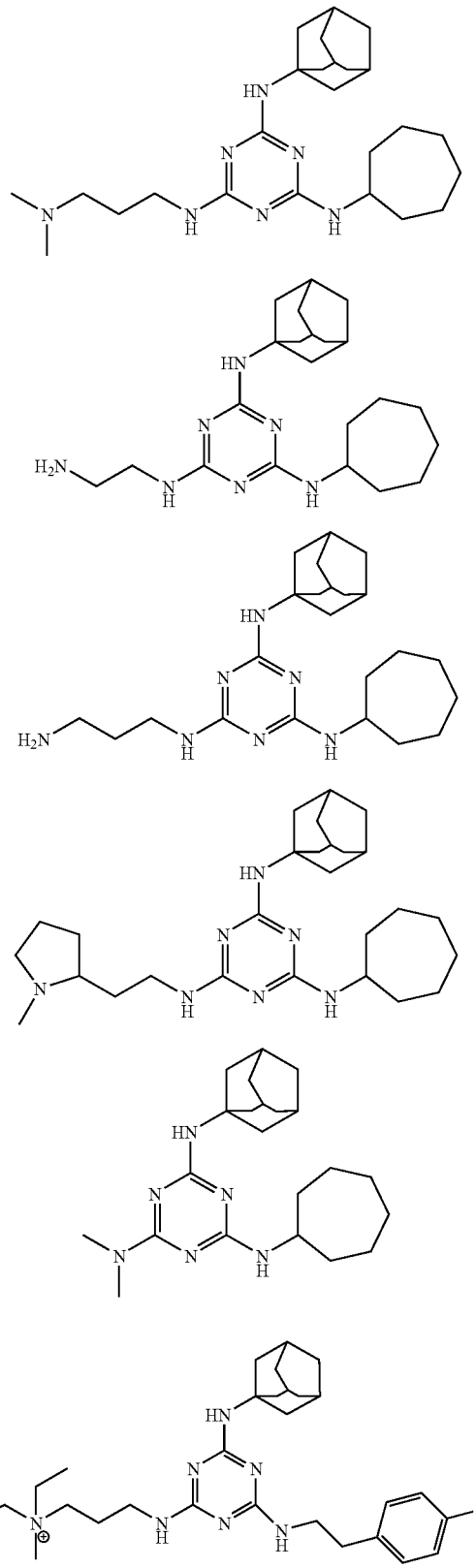
or a pharmaceutically acceptable salt thereof;
and stereoisomers, isotopic variants and tautomers thereof;
and provided the compound is not h9.

8. A compound of claim 7 wherein the compound is

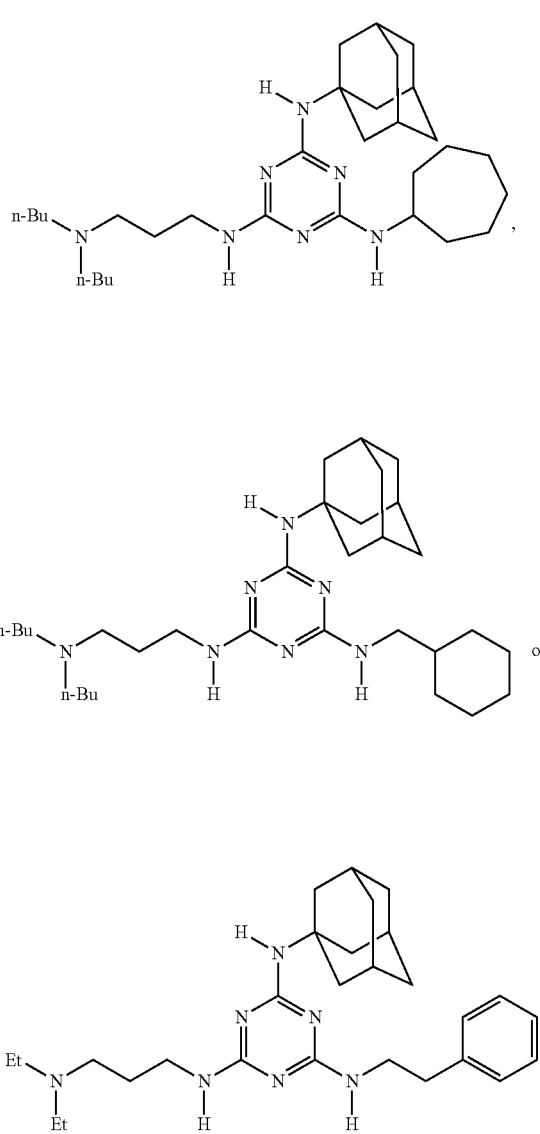

or a pharmaceutically acceptable salt thereof;

and stereoisomers, isotopic variants and tautomers thereof.

9. A compound of any one of claim 1, 4, 5, 6, or 7 wherein the compound is a quaternary salt.

10. A pharmaceutical composition comprising a pharmaceutically acceptable carrier and a pharmaceutically effective amount of a compound of any one of claim 1, 4, 5, 6, or 7.

11. The pharmaceutical composition of claim 10, wherein the carrier is selected from a topical carrier, an oral carrier, or a parenteral carrier.

12. A compound according to claim 5, wherein $R^3$ is substituted or unsubstituted methyl, ethyl, n-propyl, or n-butyl.

13. A s-triazine compound having a formula II:

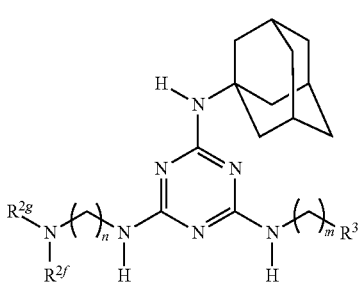

wherein
each of $R^{2f}$, and $R^{2g}$ is independently selected from hydrogen, and substituted or unsubstituted $C_1$-$C_6$ alkyl; or $R^{2f}$ and $R^{2g}$ may join together to form a cycloheteroalkyl ring of 3-7 atoms; m is 0, 1, 2, or 3; and n is 2, 3, or 4; and $R^3$ is phenyl, optionally substituted with one or more substituents independently selected from halo, alkoxy, or alkyl;

or a pharmaceutically acceptable salt thereof;

and stereoisomers, isotopic variants and tautomers thereof.

14. A compound according to claim 13, wherein $R^3$ is phenyl, substituted with Cl, OMe, methyl, ethyl, n-propyl, or n-butyl.

15. A s-triazine compound having a formula II:

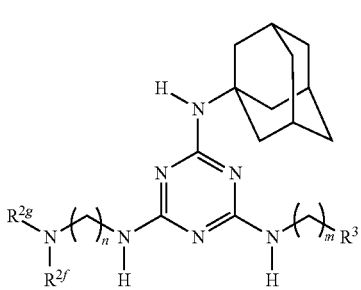

wherein
each of $R^{et}$, and $R^{2g}$ is independently selected from hydrogen, and substituted or unsubstituted $C_1$-$C_6$ alkyl; or $R^{2f}$ and $R^{2g}$ may join together to form a cycloheteroalkyl ring of 3-7 atoms; m is 0, 1, 2, or 3; and n is 2, 3, or 4; and $R^3$ is heteroaryl, optionally substituted with one or more substituents independently selected from halo, alkoxy, or alkyl;

or a pharmaceutically acceptable salt thereof;

and stereoisomers, isotopic variants and tautomers thereof.

16. A compound according to claim 15, wherein $R^3$ is pyridyl, unsubstituted or substituted with Cl, OMe, methyl, ethyl, n-propyl, or n-butyl.

17. A method for treating, ameliorating or managing a disease or condition which comprises administering to a patient in need of such treatment, amelioration or management, a therapeutically effective amount of a pharmaceutical composition of claim 10, wherein the disease or condition is or results from a bacterial infection.

* * * * *